US006884803B2

(12) United States Patent
Apodaca et al.

(10) Patent No.: US 6,884,803 B2
(45) Date of Patent: Apr. 26, 2005

(54) PHENYLALKYNES

(75) Inventors: Richard Apodaca, San Diego, CA (US); Wei Xiao, San Diego, CA (US); Jill A. Jablonowski, San Diego, CA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 10/307,870

(22) Filed: Dec. 2, 2002

(65) Prior Publication Data

US 2003/0144323 A1 Jul. 31, 2003

Related U.S. Application Data

(60) Provisional application No. 60/339,523, filed on Dec. 10, 2001.

(51) Int. Cl.$^7$ ............... C07D 403/06; C07D 295/04; A61K 31/496; A61K 31/495; A61P 25/24
(52) U.S. Cl. ............... 514/252.12; 514/252.13; 514/253.01; 514/254.1; 514/254.04; 514/254.05; 514/254.06; 544/360; 544/367; 544/366; 544/369; 544/370; 544/371; 544/374; 544/398; 544/402; 544/60; 544/106; 546/152; 546/194; 548/400; 548/570
(58) Field of Search ............... 544/360, 367, 544/369, 366, 370, 371, 374, 398, 402; 514/252.12, 252.13, 253.01, 254.1, 254.04, 254.05, 254.06

(56) References Cited

U.S. PATENT DOCUMENTS

| 5,217,986 A | 6/1993 | Pomponi et al. |
| 5,352,707 A | 10/1994 | Pompni et al. |
| 5,869,479 A | 2/1999 | Kreutner |

FOREIGN PATENT DOCUMENTS

| EP | 0978512 A1 | 2/2000 |
| WO | WO 99/42458 | 8/1999 |
| WO | WO 99/59969 A1 | 11/1999 |
| WO | WO 01/66534 A2 | 9/2001 |
| WO | WO 02/05501 A2 | 7/2002 |
| WO | WO 02/076925 A2 | 10/2002 |
| WO | WO 03/060099 A1 | 6/2003 |

OTHER PUBLICATIONS

Leurs et al. {Therapeutic potential of histamine H3 receptor agonists and antagonists: TiPS–May 1998 (vol. 19), 177–183}.*

International Search Report dated Oct. 10, 2003 for corresponding Appln. No. PCT/US03/19601.

Glase et al.: "Aryl 1–But–3–ynyl–4–phenyl–1,2,3,6–tetrahydropy ridines as Potential Antipsychotic Agents: Synthesis and Structure–Activity Relationships" Journal of Medicinal Chemistry, American Chemical Society. Washington, US, vol. 39, No. 16, Jul. 1, 1996, pp. 3179–3187, XP002092426 ISSN: 0022–2623 Scheme 1a.

Wright, J. L. et al.: "Subtype–Selectice N–Methyl–D–Aspartate Receptor Antagonists: Synthesis and Biological Evaluation of 1–(Arylalkynl)–4–Benzylpiperidines" Journal of Medicinal Chemistry, vol. 42, No. 13, 1999, pp. 2469–2477, XP002255630 Scheme 1; Table 1 compound 33.

Della, E. W. et al.: "Synthesis of Bridgehead Nitrogen Hetrocycles via Cyclization of alpha–Ammonio 5–Hexenyl Radicals" Journal of Organic Chemistry, vol. 64, No. 6, 1999, pp. 1798–1806, XP002255631 Scheme 3, preparation of compound 13 (R=H) p. 1803, right–hand column, paragraph 8.

PCT International Search Report, dated Apr. 1, 2003, for PCT Int'l. Appln. No. PCT/US02/38480.

Albengres, E. et al. Systemic Antifungal Agents. Drug Safety (Feb. 1998) 18(2):83–97.

Ali, S.M. et al. Design, Synthesis, and Structure–Activity Relationships of Acetylene–Based Histamine H3 Receptor Antagonists. J. Med. Chem. (1999) 42(5):903–909.

Arrang, J.–M. et al. Auto–inhibition of Brain Histamine Release Mediated by a Novel Class (H3) of Histamine Receptor. Nature (Apr. 1983) 302:832–837.

Ash, A.S.F.; Schild, H.O. Receptors Mediating Some Actions of Histamine. Br. J. Pharmac. Chemother. (1966) 27:427–439.

Back, D.J.; Tjia, J.F. Inhibition of Tolbutamide Metabolism by Substituted Imidazole Drugs In Vivo: Evidence for a Structure–Activity Relationship. Br. J. Pharmacol. (1985) 85:121–126.

Barnes, J.C. et al. The Selective Histamine H3 Receptor Antagonist Thioperamide Improves Cognition and Enhances Hippocampal Acetylcholine Release In Vivo. Soc. Neurosci. Abstr. (1993) 19:1813.

(Continued)

*Primary Examiner*—Mark L. Berch
*Assistant Examiner*—Kahsay Habte
(74) *Attorney, Agent, or Firm*—John Harbour

(57) ABSTRACT

Disclosed are substituted phenylalkynes of formula (I), wherein $R^1$, $R^2$, $R^3$, $R^4$, $R^5$ and n are as defined, compositions containing them, and methods of making and using them to treat histamine-mediated conditions.

23 Claims, No Drawings

OTHER PUBLICATIONS

Bioworld Today, Mar. 2, 1999, p. 3.

Black, J.W. et al. Definition and Antagonism of Histamine H2–Receptors. Nature (Apr. 1972) 236:385–390.

Ding, Y.–S. et al. Synthesis of High Specific Activity (+)– and (–)–6[18F]Fluoronorepinephrine via the Nucleophilic Aromatic Substitution Reaction. J. Med. Chem. (1991) 34(2):767–771.

Ganellin, C.R. et al. Synthesis of Potent Non–Imidazole Histamine H3–Receptor Antagonists. Arch. Pharm. Pharm. Med. Chem. (Weinheim, Ger.) (1998) 331:395–404.

Garbag, M. et al. S–[2–(4–Imidazolyl)ethyl]isothiourea, a Highly Specific and Potent Histamine H3 Receptor Agonist. J. Pharmacol. Exp. Ther. (1992) 263(1):304–310.

Gliatech Inc. Press Release Nov. 5, 1998.

Ichinose, M.; Barnes, P.J. Histamine H3–Receptors Modulate Nonadrenergic Noncholinergic Neural Bronchoconstriction in Guinea–Pig In Vivo. Eur. J. Pharmacol. (1989) 174(1):49–55.

Imamura, M. et al. Unmasking of Activated Histamine H3–Receptors in Myocardial Ischemia: Their Role as Regulators of Exocytotic Norepinephrine Release. J. Pharmacol. Exp. Ther. (1994) 271(3):1259–1266.

Kapetanovic, I.M.; Kupferberg, H.J. Nafimidone, an Imidazole Anticonvulsant, and Its Metabolite as Potent Inhibitors of Microsomal Metabolism of Phenytoin and Carbamazepine. Drug Metab. Dispos. (1984) 12(5):560–564.

Korte, A. et al. Characterization and Tissue Distribution of H3 Histamine Receptors in Guinea Pigs by N alpha–Methylhistamine. Biochem. Biophys. Res. Commun. (May 1990) 168(3):979–986.

Krause, M. et al. Medicinal Chemistry of Histamine H3 Receptor Agonists; In The Histamine H3 Receptor—A Target for New Drugs Leurs. R.; Timmerman, H. (Eds.) Elsevier (1998) 175–196.

Lavrijsen, K. et al. Induction Potential of Antifungals Containing an Imidazole or Triazole Moiety. Biochem. Pharmacol. (1986) 35(11):1867–1878.

Leurs, R. et al. The Medicinal Chemistry and Therapeutic Potentials of Ligands of the Histamine H3 Receptor. Prog. Drug Res. (1995) 45:107–165.

Lin, J.–S. et al. Involvement of Histaminergic Neurons in Arousal Mechanisms Demonstrated with H3–Receptor Ligands in the Cat. Brain Res. (1990) 523:325–330.

Linney, I.D. et al. Design, Synthesis, and Structure–Activity Relationships of Novel Non–Imidazole Histamine H3 Receptor Antagonists. J. Med. Chem. (2000) 43(12):2362–2370.

Lovenberg, T.W. et al. Cloning and Functional Expression of the Human Histamine H3 Receptor. Mol. Pharmacol. (1999) 55:1101–1107.

Lovenberg, T.W. et al. Cloning of Rat Histamine H3 Receptor Reveals Distinct Species Pharmacological Profiles. J. Pharmacol. Exp. Ther. (2000) 293(3):771–778.

Machidori, H. et al. Zucker Obese Rats: Defect in Brain Histamine Control of Feeding. Brain Res. (1992) 590:180–186.

McLeod, R.L. et al. Antimigraine and Sedative Activity of SCH 50971: A Novel Orally–Active Histamine H3 Receptor Agonist. Soc. Neurosci. Abstr. (1996) 22:2010.

Meier, G. et al. Piperidino–Hydrocarbon Compounds as Novel Non–Imidazole Histamine H3–Receptor Antagonists. Bioorg. Med. Chem. (2002) 10:2535–2542.

Monti, J.M. et al. Effects of Selective Activation or Blockade of the Histamine H3 Receptor on Sleep and Wakefulness. Eur. J. Pharmacol. (1991) 205(3):283–287.

Morisset, S. et al. High Constitutive Activity of Native H3 Receptors Regulates Histamine Neurons in Brain. Nature (Dec. 2000) 408:860–864.

Oda, T. et al. Molecular Cloning and Characterization of a Novel Type of Histamine Receptor Preferentially Expressed in Leukocytes. J. Biol. Chem. (2000) 275(47):36781–36786.

Panula, P. et al. Significant Changes in the Human Brain Histaminergic System in Alzheimer's Disease. Soc. Neurosci. Abstr. (1995) 21:1977.

Phelps, M.E. Positron Emission Tomography Provides Molecular Imaging of Biological Processes. Proc. Natl. Acad. Sci. (2000) 97(16):9226–9233.

Phillips, J.G.; Ali, S.M. Medicinal Chemistry of Histamine H3 Receptor Antagonists: In The Histamine H3 Receptor—A Target for New Drugs Leurs, R.; Timmerman, H. (Eds.) Elsevier (1998) 197–222.

Rouleau, A. et al. Bioavailability, Antinociceptive and Antiinflammatory Properties of BP 2–94, a Histamine H3 Receptor Agonist Prodrug. J. Pharmacol. Exp. Ther. (1997) 281(3):1085–1094.

Schlicker, E.; Marr, I. The Moderate Affinity of Clozapine at H3 Receptors Is Not Shared by Its Two Major Metabolites and by Structurally Related and Unrelated Atypical Neuroleptics. Naunyn–Schmiedeberg's Arch. Pharmacol. (1996) 353:290–294.

Sheets, J.J.; Mason, J.I. Ketoconazole: a Potent Inhibitor of Cytochrome P–450–Dependent Drug Metabolism in Rat Liver. Drug Metab. Dispos. (1984) 12(5):603–606.

Stark, H. et al. Developments of Histamine H3–Receptor Antagonists. Drugs Future (1996) 21(5):507–520.

Tozer, M.J.; Kalindjian, S.B. Histamine H3 Receptor Antagonists. Exp. Opin. Ther. Patents (2000) 10(7):1045–1055.

Walczynski, K. et al. Non–Imidazole Histamine H3 Ligands, Part 2: New 2–Substituted Benzothiazoles as Histamine H3 Antagonists. Arch. Pharm. Pharm. Med. Chem. (Weinheim, Ger.) (1999) 332:389–398.

Walczynski, K. et al. Non–Imidazole Histamine H3 Ligands. Part I. Synthesis of 2–(1–Piperazinyl)– and 2–(Hexahydro–1H–1,4–diazepin–1–yl)benzothiazole Derivatives as H3–Antagonists with H1 Blocking Activities. Farmaco (1999) 54:684–694.

West, R.E. et al. Identification of Two H3–Histamine Receptor Subtypes. Mol. Pharmacol. (1990) 38(5):610–613.

West, R.E., Jr. et al. The Profiles of Human and Primate [3H]N alpha–methylhistamine Binding Differ from That of Rodents. Eur. J. Pharmacol. (1999) 377:233–239.

Yokoyama, H. et al. Effect of Thioperamide, a Histamine H3 Receptor Antagonist, on Electrically Induced Convulsions in Mice. Eur. J. Pharmacol. (1993) 234:129–133.

\* cited by examiner

PHENYLALKYNES

This application claims the benefit of U.S. Provisional Application No. 60/339,523, filed Dec. 10, 2001.

FIELD OF THE INVENTION

The present invention relates to phenylalkynes, their synthesis and their use, for example, for the treatment of disorders and conditions mediated by the histamine receptor.

BACKGROUND OF THE INVENTION

Histamine [2-(imidazol-4-yl)ethylamine] is a transmitter substance. Histamine exerts a physiological effect via multiple distinct G-protein coupled receptors. It plays a role in immediate hypersensitivity reactions and is released from mast cells following antigen IgE antibody interaction. The actions of released histamine on the vasculature and smooth muscle system account for the symptoms of the allergic response. These actions occur at the $H_1$ receptor (Ash, A. S. F. and Schild, H. O., *Br. J. Pharmac. Chemother.* 1966, 27:427–439) and are blocked by the classical antihistamines (e.g. diphenhydramine). Histamine is also an important regulator of gastric acid secretion through its action on parietal cells. These effects of histamine are mediated via the $H_2$ receptor (Black, J. W. et al., *Nature* 1972, 236:385–390) and are blocked by $H_2$ receptor antagonists (e.g. cimetidine). The third histamine receptor -$H_3$- was first described as a presynaptic autoreceptor in the central nervous system (CNS) (Arrang, J.-M. et al., *Nature* 1983, 302:832–837) controlling the synthesis and release of histamine. Recent evidence has emerged showing that the $H_3$ receptors are also located presynaptically as heteroreceptors on serotonergic, noradrenergic, dopaminergic, cholinergic, and GABAergic (gamma-aminobutyric acid containing) neurons. These $H_3$ receptors have also recently been identified in peripheral tissues such as vascular smooth muscle. Consequently there are many potential therapeutic applications for histamine $H_3$ agonists, antagonists, and inverse agonists. (See: *"The Histamine $H_3$ Receptor-A Target for New Drugs"*, Leurs, R., and Timmerman, H., (Eds.), Elsevier, 1998; Morisset, S. et al., *Nature* 2000, 408:860–864.) A fourth histamine receptor -$H_4$- was recently described by Oda, T. et al. (*J. Biol. Chem.* 2000, 275(47):36781–36786).

The potential use of histamine $H_3$ agonists in sleep/wake and arousal/vigilance disorders is suggested based on animal studies (Lin, J.-S. et al., *Brain Res.* 1990, 523:325–330; Monti, J. M. et al., *Eur. J. Pharmacol.* 1991, 205:283–287). Their use in the treatment of migraine has also been suggested (McLeod, R. L. et al., *Soc. Neurosci. Abstr.* 1996, 22:2010) based on their ability to inhibit neurogenic inflammation. Other applications could be a protective role in myocardial ischemia and hypertension where blockade of norepinephrine release is beneficial (Imamura, M. et al., *J. Pharmacol. Exp. Ther.* 1994, 271(3):1259–1266). It has been suggested that histamine $H_3$ agonists may be beneficial in asthma due to their ability to reduce non-adrenergic non-cholinergic (NANC) neurotransmission in airways and to reduce microvascular leakage (Ichinose, M. and Barnes, P. J., *Eur. J. Pharmacol.* 1989, 174:49–55).

Several indications for histamine $H_3$ antagonists and inverse agonists have similarly been proposed based on animal pharmacology experiments with known histamine $H_3$ antagonists (e.g. thioperamide). These include dementia, Alzheimer's disease (Panula, P. et al., *Soc. Neurosci. Abstr.* 1995, 21:1977), epilepsy (Yokoyama, H. et al., *Eur. J. Pharmacol.* 1993, 234:129–133), narcolepsy, eating disorders (Machidori, H. et al., *Brain Res.* 1992, 590:180–186), motion sickness, vertigo, attention deficit hyperactivity disorders (ADHD), learning and memory (Barnes, J. C. et al., *Soc. Neurosci. Abstr.* 1993, 19:1813), and schizophrenia (Schlicker, E. and Marr, I., *Naunyn-Schmiedeberg's Arch. Pharmacol.* 1996, 353:290–294). (Also see: Stark, H. et al., *Drugs Future* 1996, 21(5):507–520; and Leurs, R. et al., *Prog. Drug Res.* 1995, 45:107–165 and references cited therein.) Histamine $H_3$ antagonists, alone or in combination with a histamine $H_1$ antagonist, are reported to be useful for the treatment of upper airway allergic response (U.S. Pat. Nos. 5,217,986; 5,352,707 and 5,869,479). Recently, a histamine $H_3$ antagonist (GT-2331) was identified and is being developed by Gliatech Inc. (Gliatech Inc. Press Release Nov. 5, 1998; *Bioworld Today*, Mar. 2, 1999) for the treatment of CNS disorders.

As noted, the prior art related to histamine $H_3$ ligands has been comprehensively reviewed (*"The Histamine $H_3$ Receptor-A Target for New Drugs"*, Leurs, R., and Timmerman, H., (Eds.), Elsevier, 1998). Within this reference the medicinal chemistry of histamine $H_3$ agonists and antagonists was reviewed (see: Krause, M. et al., and Phillips, J. G. and Ali, S. M., respectively). The importance of an imidazole moiety containing only a single substitution in the 4 position was noted together with the deleterious effects of additional substitution on activity. Particularly methylation of the imidazole ring at any of the remaining unsubstituted positions was reported to strongly decrease activity. Additional publications support the hypothesis that an imidazole function is essential for high affinity histamine $H_3$ receptor ligands (see: Ali, S. M. et al., *J. Med. Chem.* 1999, 42:903–909, and Stark, H. et al., and references cited therein). However many imidazole-containing compounds are substrates for histamine methyl transferase, the major histamine metabolizing enzyme in humans, which leads to shortened half-lives and lower bioavailability (see: Rouleau, A. et al., *J. Pharmacol. Exp. Ther.* 1997, 281(3):1085–1094). In addition, imidazole-containing drugs, via their interaction with the cytochrome P450 monooxygenase system, can result in unfavorable biotransformations due to enzyme induction or enzyme inhibition (see: Kapetanovic, I. M. and Kupferberg, H. J., *Drug Metab. Dispos.* 1984, 12(5):560–564; Sheets, J. J. and Mason, J. I., *Drug Metab. Dispos.* 1984, 12(5):603–606; Back, D. J. and Tjia, J. F., *Br. J. Pharmacol.* 1985, 85:121–126; Lavrijsen, K. et al., *Biochem. Pharmacol.* 1986, 35(11):1867–1878; Albengres, E. et al., *Drug Safety* 1998, 18(2):83–97). The poor blood-brain barrier penetration of earlier histamine $H_3$ receptor ligands may also be associated with the imidazole fragment (Ganellin, C. R. et al., *Arch. Pharm. Pharm. Med. Chem.* (Weinheim, Ger.) 1998, 331:395–404).

More recently, several publications have described histamine $H_3$ ligands that do not contain an imidazole moiety, for example: Ganellin, C. R. et al.; Walczynski, K. et al., *Arch. Pharm. Pharm. Med. Chem.* (Weinheim, Ger.) 1999, 332:389–398; Walczynski, K. et al., *Farmaco* 1999, 54:684–694; Linney, I. D. et al., *J. Med. Chem.* 2000, 43:2362–2370; Tozer, M. J. and Kalindjian, S. B., *Exp. Opin. Ther. Patents* 2000,10:1045–1055; U.S. Pat. No. 5,352,707; PCT Application WO 99/42458; PCT Application WO 02/076925; and EP Application 0978512, Feb. 9, 2000.

The compounds of the present invention do not contain the imidazole moiety, and its inherent liabilities, and yet maintain potency at the human $H_3$ receptor as determined by receptor binding to the human histamine $H_3$ receptor (see: Lovenberg, T. W. et al., *Mol. Pharmacol.* 1999, 55:1101–1107). Screening using the human receptor is particularly important for the identification of new therapies for the treatment of human disease. Conventional binding assays, for example, are determined using rat synaptosomes (Garbarg, M. et al., *J. Pharmacol. Exp. Ther.* 1992, 263(1) :304–310), rat cortical membranes (West, R. E. et al., *Mol. Pharmacol.* 1990, 38:610–613), and guinea pig brain (Korte, A. et al., *Biochem. Biophys. Res. Commun.* 1990, 168(3):979–986). Only limited studies have been performed previously using human tissue but these allude to significant differences in the pharmacology of rodent and primate receptors (West, R. E. et al., *Eur. J. Pharmacol.* 1999, 377:233–239).

We now describe a series of phenylalkynes with the ability to modulate the activity of the histamine receptor, specifically the $H_3$ receptor, without the inherent problems associated with the presence of an imidazolyl moiety.

SUMMARY OF THE INVENTION

The present invention is directed to pharmaceutically active phenylalkynes, methods of making them, and methods of using them. The invention features a compound of formula (I)

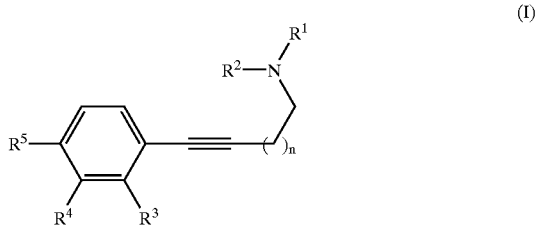

wherein n is an integer from 0 to 1;
$R^1$ and $R^2$ are independently selected from $C_{1-3}$ alkyl, allyl, and $C_{3-8}$ cycloalkyl, or taken together with the nitrogen to which they are attached, they form a non-aromatic 4–7 membered heterocyclyl optionally including up to two additional heteroatoms independently selected from O, S, and N;
one of $R^3$, $R^4$, and $R^5$ is G, one of the remaining two is hydrogen, and the other is selected from hydrogen, fluoro, and chloro;
G is $L^2Q$;
$L^2$ is methylene;
Q is $NR^8R^9$ wherein $R^8$ is independently selected from hydrogen, $C_{1-6}$ alkyl, $C_{3-6}$ alkenyl, 6–9 membered carbocyclyl, 3–12 membered heterocyclyl (preferably 5–9 or 5–8-membered heterocyclyl), phenyl, (5–9-membered heterocyclyl)$C_{1-6}$ alkylene, and (phenyl) $C_{1-6}$ alkylene; and $R^9$ is independently selected from $C_{1-6}$ alkyl, $C_{3-6}$ alkenyl, 6–9 membered carbocyclyl, 3–12 membered heterocyclyl (preferably 5–9 or 5–8-membered heterocyclyl), phenyl, (5–9-membered heterocyclyl)$C_{1-6}$ alkylene, and (phenyl) $C_{1-6}$ alkylene;
or
Q is a saturated 3–13 membered N-linked heterocyclyl, wherein, in addition to the N-linking nitrogen, the 3–13 membered heterocyclyl may optionally contain between 1 and 3 additional heteroatoms independently selected from O, S, and N;
wherein each of the above alkyl, alkylene, alkenyl, heterocyclyl, cycloalkyl, carbocyclyl, and aryl groups of Formula (I) may each be independently and optionally substituted with between 1 and 3 substituents independently selected from methoxy, halo, amino, nitro, hydroxyl, and $C_{1-3}$ alkyl;

and wherein 1–3 substituents of Q can be further independently selected (in addition to the preceding paragraph) from tert-butyloxycarbonyl, carboxamide, $C_{1-6}$ alkyl, 5–9-membered heterocyclyl, $N(C_{1-6}$ alkyl)(5–9 membered heterocyclyl), NH(5–9 membered heterocyclyl), O(5–9 membered heterocyclyl), (5–9 membered heterocyclyl)$C_{1-3}$ alkylene, phenyl, $C_{1-2}$-hydroxyalkylene, $C_{2-6}$ alkoxy, ($C_{3-6}$ cycloalkyl)-O—, phenyl, (phenyl)$C_{1-3}$ alkylene, and (phenyl)$C_{1-3}$ alkylene-O— and where said substituent groups of Q may optionally have between 1 and 3 substituents independently selected from trifluoromethyl, halo, nitro, cyano, and hydroxy;
or a pharmaceutically acceptable salt, ester, or amide thereof.

The invention also features a pharmaceutical composition comprising a compound of the invention and a pharmaceutically acceptable carrier; and methods of preparing or formulating such compositions. A composition of the invention may further include more than one compound of the invention, or a combination therapy (combination formulation or combination of differently formulated active agents).

The invention also provides methods of treating certain conditions and diseases, each of which methods includes administering a therapeutically effective (or jointly effective) amount of a compound or composition of the invention to a subject in need of such treatment. The disclosed compounds are useful in methods for treating or preventing neurologic disorders including sleep/wake and arousal/vigilance disorders (e.g. insomnia and jet lag), attention deficit hyperactivity disorders (ADHD), learning and memory disorders, cognitive dysfunction, migraine, neurogenic inflammation, dementia, mild cognitive impairment (pre-dementia), Alzheimer's disease, epilepsy, narcolepsy, eating disorders, obesity, motion sickness, vertigo, schizophrenia, substance abuse, bipolar disorders, manic disorders and depression, as well as other histamine $H_3$ receptor mediated disorders such as upper airway allergic response, asthma, itch, nasal congestion and allergic rhinitis in a subject in need thereof. For example, the invention features methods for preventing, inhibiting the progression of, or treating upper airway allergic response, asthma, itch, nasal congestion and allergic rhinitis.

In yet another embodiment, the disclosed compounds may be used in a combination therapy method including administering a jointly effective dose of an $H_3$ antagonist and administering a jointly effective dose of a histamine $H_1$ antagonist, such as loratidine (CLARITIN™), desloratidine (CLARINEX™), fexofenadine (ALLEGRA™) and cetirizine (ZYRTEC™), for the treatment of allergic rhinitis, nasal congestion, and allergic congestion.

In yet another embodiment, the disclosed compounds may be used in a combination therapy method, including administering a jointly effective dose of an $H_3$ antagonist and administering a jointly effective dose of a neurotransmitter re-uptake blocker, such as a selective serotonin re-uptake inhibitor (SSRI) or a non-selective serotonin, dopamine or norepinephrine re-uptake inhibitor, including fluoxetine (PROZAC™), sertraline (ZOLOFT™), paroxetine (PAXIL™) and amitryptyline, for the treatment of depression, mood disorders or schizophrenia.

Additional features and advantages of the invention will become apparent from the detailed description and examples below, and the appended claims.

DETAILED DESCRIPTION OF THE INVENTION

The present invention provides phenylalkyne compounds useful for the treatment of disorders and conditions modulated by a histamine receptor.

A. Terms

Certain terms are defined below and by their usage throughout this disclosure.

As used herein, "halo" or "halogen" shall mean monovalent radicals of chlorine, bromine, fluorine and iodine.

As used herein, the term "alkyl", whether used alone or as part of a substituent group, shall include straight and branched carbon chains. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1–4 carbon atoms. "Alkylene" refers to a bivalent hydrocarbyl group, such as methylene (CH$_2$), ethylene (—CH$_2$—CH$_2$—) or propylene (—CH$_2$CH$_2$CH$_2$—), and so on.

As used herein, unless otherwise noted, "alkenyl" shall mean a straight or branched hydrocarbon group with at least two hydrogen atoms replaced with a pi bond to form a carbon-carbon double bond, such as propenyl, butenyl, pentenyl, and so on. Where the alkenyl group is R$^8$ or R$^9$, the open radical (point of attachment to the rest of the molecule) is on sp$^3$ carbon, as illustrated by allyl, and the double bond or bonds is therefore at least alpha (if not beta, gamma, etc.) to the open radical.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, unless otherwise noted, "cycloalkyl" shall denote a three- to eight-membered, saturated monocyclic carbocyclic ring structure. Suitable examples include cyclopropyl, cyclobutyl, cyclopentyl, cyclohexyl, cycloheptyl and cyclooctyl.

As used herein, unless otherwise noted, "cycloalkenyl" shall denote a three- to eight-membered, partially unsaturated, monocyclic, carbocyclic ring structure, wherein the ring structure contains at least one double bond. Suitable examples include cyclohexenyl, cyclopentenyl, cycloheptenyl, cyclooctenyl, cyclohex-1,3-dienyl and the like.

As used herein, unless otherwise noted, "aryl" shall refer to carbocyclic aromatic groups such as phenyl, naphthyl, and the like. Divalent radicals include phenylene (—C$_6$H$_4$—) which is preferably phen-1,4-diyl, but may also be phen-1,3-diyl.

As used herein, unless otherwise noted, "aralkyl" shall mean any alkyl group substituted with an aryl group such as phenyl, naphthyl and the like. Examples of aralkyls include benzyl, phenethyl, and phenylpropyl.

As used herein, unless otherwise noted, "carbocyclyl" shall mean any cyclic group consisting of 3–13 carbon atoms, and preferably 6–9 carbon atoms, in the skeleton ring or rings, if the carbocycle is a fused or spiro bicyclic or tricyclic group. A carbocycle may be saturated, unsaturated, partially unsaturated, or aromatic. Examples include cycloalkyl, cycloalkenyl, cycloalkynyl; specific examples include phenyl, benzyl, indanyl, and biphenyl. A carbocycle may have substituents that are not carbon or hydrogen, such as hydroxy, halo, halomethyl, and so on as provided elsewhere herein.

As used herein, unless otherwise noted, the terms "heterocycle", "heterocyclyl" and "heterocyclo" shall denote any three-, four-, five-, six-, seven-, or eight-membered monocyclic, eight or nine or ten or eleven membered bicyclic or twelve or thirteen or fourteen membered tricyclic ring structure containing at least one heteroatom moiety selected from the group consisting of N, O, SO, SO$_2$, (C=O), and S, and preferably N, O, or S, optionally containing one to four additional heteroatoms in each ring. In some embodiments, the heterocyclyl contains between 1 and 3 or between 1 and 2 additional heteroatoms. Unless otherwise specified, a heterocyclyl may be saturated, partially unsaturated, aromatic or partially aromatic. The heterocyclyl group may be attached at any heteroatom or carbon atom, which results in the creation of a stable structure.

Exemplary monocyclic heterocyclic groups can include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazaolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, hexahydroazepinyl, 4-piperidinyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dixolane and tetrahydro-1,1-dioxothienyl, dioxanyl, isothiazolidinyl, thietanyl, thietanyl, triazinyl, triazolyl, tetrazolyl, azetidinyl and the like.

For example, where Q is a saturated 3–13 membered N-linked heterocyclyl, Q necessarily contains at least one nitrogen, and the carbon atoms are sp$^3$ hybridized.

In general, exemplary bicyclic heterocyclyls include benzthiazolyl, benzoxazolyl, benzoxazinyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopridyl, furopyridinyl (such as furo[2,3-c]pyridinyl, furo[3,1-b]pyridinyl), or furo[2,3-b]pyridinyl), dihydroisoindolyl, dihydroquinazolinyl (such as 3,4-dihydro-4-oxo-quinazolinyl), tetrahydroquinolinyl (such as 1,2,3,4-tetrahydroquinolinyl), tetrahydroisoquinolinyl (such as 1,2,3,4-tetrahydroisoquinolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isoindolyl, tetrahydroindoazolyl (such as 4,5,6,7-tetrahydroindoazolyl), isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl,

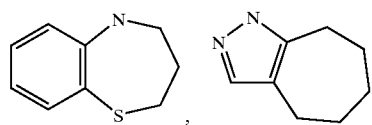, and the like.

Exemplary tricyclic heterocylclic groups include acridinyl, phenoxazinyl, phenazinyl, phenothiazinyl, carbozolyl, pyrimidinyl, phenanthrolinyl, carbolinyl, naphthothienyl, thianthrenyl, and the like.

Preferred heterocyclyl groups include morpholinyl, piperidinyl, piperazinyl, pyrrolidinyl, pyrimidinyl, pyridyl, pyrrolyl, imidazolyl, oxazolyl, isoxazolyl, acridinyl, azepinyl, hexahydroazepinyl, azetidinyl, indolyl, isoindolyl, thiazolyl, thiadiazolyl, quinolinyl, isoquinolinyl, 1,2,3,4-tetrahydroquinolinyl, 1,3,4-trihydroisoquinolinyl, 4,5,6,7- tetrahydroindadolyl, benzoxazinyl, benzoxazolyl, benzthiazolyl, benzimidazolyl, tetrazolyl, oxadiazolyl,

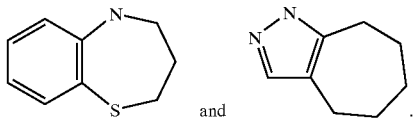
and

As used herein, unless otherwise noted, the term "heterocyclyl-alkyl" or "heterocyclyl-alkylene" shall denote any alkyl group substituted with a heterocyclyl group, wherein the heterocyclyl-alkyl group is bound through the alkyl portion to the central part of the molecule. Suitable examples of heterocyclyl-alkyl groups include, but are not limited to piperidinylmethyl, pyrrolidinylmethyl, piperidinylethyl, piperazinylmethyl, pyrrolylbutyl, piperidinylisobutyl, pyridylmethyl, pyrimidylethyl, and the like.

When a particular group is "substituted" (e.g., alkyl, alkylene, cycloalkyl, aryl, heterocyclyl, heteroaryl), that group may have one or more substituents, preferably from one to five substituents, more preferably from one to three substituents, most preferably from one to two substituents, independently selected from the list of substituents.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Under standard nomenclature used throughout this disclosure, the terminal portion of the designated side chain is described first, followed by the adjacent functionality toward the point of attachment. Thus, for example, a "phenyl (alkyl)amido(alkyl)" substituent refers to a group of the formula

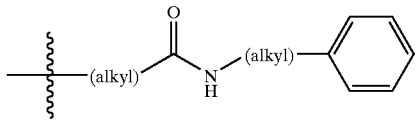

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes prevention, inhibition of onset, or alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Abbreviations used in the specification, particularly in the Schemes and Examples, are as follows:

| | |
|---|---|
| DBAD | Di-tert-butyl azodicarboxylate |
| DCE | 1,2-dichloroethane |
| DCM | Dichloromethane |
| DEAD | Diethyl azodicarboxylate |
| DMA | N,N-dimethylacetamide |
| DMAP | 4-N,N-dimethylamino-pyridine |
| DME | 1,2-dimethoxyethane |
| DMF | Dimethylformamide |
| DMSO | Dimethylsulfoxide |
| RT | Room temperature |
| TEA | Triethylamine |
| TFA | Trifluoroacetic acid |
| THF | Tetrahydrofuran |

The next section describes the compounds provided by the invention in more detail.

B. Compounds

The invention features compounds of formula (I) as described, for example, in the above Summary section and in the claims. Preferred compounds include those wherein:

(a) $NR^1R^2$ taken together form piperidinyl, methylpiperidinyl, dimethylamino, pyrrolidinyl, diethylamino, methylethylamino, ethylpropylamino, or dipropylamino;

(b) $NR^1R^2$ taken together form piperidinyl, pyrrolidinyl, or diethylamino;

(c) $NR^1R^2$ taken together form piperidinyl or pyrrolidinyl;

(d) one of $R^4$ and $R^5$ is G;

(e) $R^4$ is G;

(f) $R^5$ is G;

(g) n is 1;

(h) Q is a saturated N-linked nitrogen-containing heterocyclyl;

(i) Q is selected from substituted or unsubstituted piperidinyl, substituted or unsubstituted piperazinyl, pyrrolinyl, pyrrolidinyl, thiomorpholinyl, and morpholinyl;

(j) substituted Q is selected from N-($C_{1-6}$ alkyl) piperazinyl, N-phenyl-piperazinyl, 1,3,8-triaza-spiro[4.5] decyl, and 1,4-dioxa-8-aza-spiro[4.5]decyl;

(k) Q is a monovalent radical of an amine selected from aziridine, 1,4,7-trioxa-10-aza-cyclododecane, thiazolidine, 1-phenyl-1,3,8-triaza-spiro[4.5]decan-4-one, piperidine-3-carboxylic acid diethylamide, 1,2,3,4,5,6-hexahydro-[2,3'] bipyridinyl, 4-(3-trifluoromethyl-phenyl)-piperazine, 2-piperazin-1-yl-pyrimidine, piperidine-4-carboxylic acid amide, methyl-(2-pyridin-2-yl-ethyl)-amine, [2-(3,4-dimethoxy-phenyl)-ethyl]-methyl-amine, thiomorpholinyl, allyl-cyclopentyl-amine, [2-(1H-indol-3-yl)-ethyl]-methyl-amine, 1-piperidin-4-yl-1,3-dihydro-benzoimidazol-2-one, 2-(piperidin-4-yloxy)-pyrimidine, piperidin-4-yl-pyridin-2-yl-amine, phenylamine, and pyridin-2-ylamine;

(l) Q is selected from N-morpholinyl and N-piperidinyl, optionally substituted with between 1 and 3 substituents independently selected from hydroxyl, carboxamide, $C_{1-6}$ alkyl, 5–9 membered or 6–9 membered heterocyclyl, N($C_{1-6}$ alkyl)(5–9 membered or 6–9 membered heterocyclyl), NH(5–9 membered or 6–9 membered heterocyclyl), (5–9 membered or 6–9 membered heterocyclyl)$C_{1-3}$ alkylene, 5–9 membered or 6–9 membered heterocyclyl-O—, $C_{1-6}$ alkoxy, ($C_{3-6}$ cycloalkyl)-O—, phenyl, (phenyl)$C_{1-3}$ alkylene, and (phenyl)$C_{1-3}$ alkylene-O— where each of above heterocyclyl, phenyl, and alkyl groups may be optionally substituted with from 1 to 3 substituents independently selected from halogen, nitro, cyano, and $C_{1-3}$ alkyl;

(m) Q is substituted with a substituent comprising a 5–9 membered or 6–9 membered heterocyclyl group selected from: pyridyl, pyrimidyl, furyl, thiofuryl, imidazolyl, (imidazolyl)$C_{1-6}$ alkylene, oxazolyl, thiazolyl, 2,3-dihydroindolyl, benzimidazolyl, 2-oxobenzimidazolyl, (tetrazolyl) $C_{1-6}$ alkylene, tetrazolyl, (triazolyl)$C_{1-6}$ alkylene, triazolyl, (pyrrolyl)$C_{1-6}$ alkylene, and pyrrolyl;

(n) Q is a substituted or unsubstituted N-morpholinyl;

(o) $R^8$ is hydrogen;

(p) $R^9$ is selected from phenyl or 5–9 membered aromatic heterocyclyl, wherein said phenyl or aromatic heterocyclyl is optionally substituted with 1–3 substituents selected from halo, nitro, cyano, and $C_{1-3}$ alkyl;

(q) $R^9$ is selected from substituted or unsubstituted phenyl, pyridyl, pyrimidyl, furyl, thiofuryl, imidazolyl, (imidazolyl)$C_{1-6}$ alkylene, oxazolyl, thiazolyl, 2,3-dihydroindolyl, benzimidazolyl, 2-oxobenzimidazolyl, (tetrazolyl) $C_{1-6}$ alkylene, tetrazolyl, (triazolyl)$C_{1-6}$ alkylene, triazolyl, (pyrrolyl)$C_{1-6}$ alkylene, and pyrrolyl;

(r) $R^9$ is substituted or unsubstituted phenyl;

(s) $R^9$ is substituted or unsubstituted pyridyl;

(t) wherein n is 1; $R^1$ and $R^2$ are independently selected from $C_2$ alkyl, or taken together with the nitrogen to which they are attached, they form a non-aromatic 5–6 membered heterocyclyl optionally including an additional heteroatom independently selected from O, S, and N; one of $R^3$, $R^4$, and $R^5$ is G and the two remaining are H; G is $L^2Q$; $L^2$ is methylene; Q is $NR^8R^9$ wherein $R^8$ is independently selected from hydrogen, $C_{1-2}$ alkyl, $C_3$ alkenyl, 6–9 membered carbocycle, 3–12 membered heterocyclyl (preferably 5–9 or 6–9), phenyl, (5–9-membered heterocyclyl)$C_{1-6}$ alkylene, and (phenyl) $C_{1-6}$ alkylene; and $R^9$ is independently selected from $C_{1-2}$ alkyl, $C_3$ alkenyl, 5–9 membered carbocyclyl, 3–12 membered heterocyclyl (for example, 5–9 membered or 6–9 membered heterocyclyl, and in some cases preferably 6-membered), phenyl, (5–9-membered heterocyclyl)$C_{1-6}$ alkylene, and (phenyl) $C_{1-6}$ alkylene; or Q is a saturated 3–13 membered N-linked heterocyclyl (preferably 5–9 or 6–9), wherein, in addition to the N-linking nitrogen, the 3–13 membered heterocyclyl may optionally contain between 1 and 3 additional heteroatoms independently selected from O, S, and N; wherein each of the above alkyl, alkylene, alkenyl, alkenylene, heterocyclyl, cycloalkyl, and aryl groups may each be independently and optionally substituted with between 1 and 3 substituents independently selected from methoxy, halo, amino, nitro, hydroxyl, and $C_{1-3}$ alkyl; and wherein substituents of Q can be further independently selected from tert-butyloxycarbonyl, carboxamide, 6–9-membered heterocyclyl, NH(6-membered heterocyclyl), O(6-membered heterocyclyl), phenyl, $C_2$-hydroxyalkylene, hydroxy, and benzyl, and,where each of above heterocyclyl, phenyl, and alkyl substituent groups of Q may be optionally substituted with trifluoromethyl; or a pharmaceutically acceptable salt, ester, or amide thereof;

(u) (1) $NR^1R^2$ taken together form piperidinyl, pyrrolidinyl, or diethylamino, and (2) Q is selected from substituted or unsubstituted piperidinyl, piperazinyl, pyrrolinyl, pyrrolidinyl, thiomorpholinyl, and morpholinyl;

(v) (1) $NR^1R^2$ taken together form piperidinyl or pyrrolidinyl, (2) n is 1, and (3) Q is selected from morpholinyl and piperidinyl;

(w) Q is morpholinyl or substituted morpholinyl;

(x) $NR^1R^2$ taken together form piperidinyl, pyrrolidinyl, or diethylamino, n is 1, and wherein Q is $NR^8R^9$ and $R^8$ is H and $R^9$ is selected from phenyl or aromatic 5–9 membered heterocyclyl, wherein said phenyl or heterocyclyl is optionally substituted with 1–3 substituents selected from halo, nitro, cyano, and $C_{1-3}$ alkyl; or (y) or combinations of the above.

Examples of compounds of the invention include: 1-[4-(4-piperidin-1-ylmethyl-phenyl)-but-3-ynyl]-piperidine; 1-[3-(4-piperidin-1-yl-but-1-ynyl)-benzyl]-piperidine; 4-[3-(4-piperidin-1-yl-but-1-ynyl)-benzyl]-morpholine; 4-[3-(4-piperidin-1-yl-but-1-ynyl)-benzyl]-morpholine dihydrochloride; 1-[4-(4-pyrrolidin-1-yl-but-1-ynyl)-benzyl]-piperidine; diethyl-[4-(4-piperidin-1-ylmethyl-phenyl)-but-3-ynyl]-amine; 4-[4-(4-piperidin-1-ylmethyl-phenyl)-but-3-ynyl]-thiomorpholine; 4-[4-(4-piperidin-1-ylmethyl-phenyl)-but-3-ynyl]-morpholine; 1-methyl-4-[4-(4-piperidin-1-ylmethyl-phenyl)-but-3-ynyl]-piperazine; 1-[4-(4-pyrrolidin-1-ylmethyl-phenyl)-but-3-ynyl]-piperidine; 4-[4-(4-piperidin-1-yl-but-1-ynyl)-benzyl]-morpholine; diethyl-[4-(4-piperidin-1-yl-but-1-ynyl)-benzyl]-amine; 1-{4-[4-(4-benzyl-piperidin-1-ylmethyl)-phenyl]-but-3-ynyl}-piperidine; 1-[4-(4-piperidin-1-yl-but-1-ynyl)-benzyl]-piperidin-4-ol; 2-{1-[4-(4-piperidin-1-yl-but-1-ynyl)-benzyl]-piperidin-2-yl}-ethanol; 1-[4-(4-piperidin-1-yl-but-1-ynyl)-benzyl]-decahydro-quinoline; 1-[4-(4-piperidin-1-yl-but-1-ynyl)-benzyl]-piperidine-4-carboxylic acid amide; 8-[4-(4-piperidin-1-yl-but-1-ynyl)-benzyl]-1,4-dioxa-8-aza-spiro[4.5]decane; 1-methyl4-[4-(4-piperidin-1-yl-but-1-ynyl)-benzyl]-piperazine; cyclohexyl-[4-(4-piperidin-1-yl-but-1-ynyl)-benzyl]-amine; indan-1-yl-[4-(4-piperidin-1-yl-but-1-ynyl)-benzyl]-amine; 1-phenyl-4-[4-(4-piperidin-1-yl-but-1-ynyl)-benzyl]-piperazine; 1-benzyl-4-[4-(4-piperidin-1-yl-but-1-ynyl)-benzyl]-piperazine; 4-[4-(4-piperidin-1-yl-but-1-ynyl)-benzyl]-piperazine-1-carboxylic acid tert-butyl ester; 1-[4-(4-piperidin-1-yl-but-1-ynyl)-benzyl]-piperazine; 1-isopropyl4-[4-(4-piperidin-1-yl-but-1-ynyl)-benzyl]-piperazine; 1-phenyl-8-[3-(4-piperidin-1-yl-but-1-ynyl)-benzyl]-1,3,8-triaza-spiro[4.5] decan-4-one; 1-[3-(4-piperidin-1-yl-but-1-ynyl)-benzyl]-piperidine-3-carboxylic acid diethylamide; 1-[3-(4-piperidin-1-yl-but-1-ynyl)-benzyl]-1,2,3,4,5,6-hexahydro-[2,3']bipyridinyl; 1-[3-(4-piperidin-1-yl-but-1-ynyl)-benzyl] 4-(3-trifluoromethyl-phenyl)-piperazine; 2-{4-[3-(4-piperidin-1-yl-but-1-ynyl)-benzyl]-piperazin-1-yl}-pyrimidine; 1-[3-(4-piperidin-1-yl-but-1-ynyl)-benzyl]-piperidine-4-carboxylic acid amide; methyl-[3-(4-piperidin-1-yl-but-1-ynyl)-benzyl]-(2-pyridin-2-yl-ethyl)-amine; [2-(3,4-dimethoxy-phenyl)-ethyl]-methyl-[3-(4-piperidin-1-yl-but-1-ynyl)-benzyl]-amine; 4-[3-(4-piperidin-1-yl-but-1-ynyl)-benzyl]-thiomorpholine; allyl-cyclopentyl-[3-(4-piperidin-1-yl-but-1-ynyl)-benzyl]-amine; 10-[3-(4-piperidin-1-yl-but-1-ynyl)-benzyl]-1,4,7-trioxa-10-aza-cyclododecane; 1-[4-(3-thiazolidin-3-ylmethyl-phenyl)-but-3-ynyl]-piperidine; [2-(1H-indol-3-yl)-ethyl]-methyl-[3-(4-piperidin-1-yl-but-1-ynyl)-benzyl]-amine; 1-{1-[3-(4-piperidin-1-yl-but-1-ynyl)-benzyl]-piperidin-4-yl}-1,3-dihydro-benzoimidazol-2-one; phenyl-[3-(4-piperidin-1-yl-but-1-ynyl)-benzyl]-amine; 1-[4-(3-pyrrolidin-1-ylmethyl-phenyl)-but-3-ynyl]-piperidine; 1-[3-(4-piperidin-1-yl-but-1-ynyl)-benzyl]-azacyclotridecane; dimethyl-[4-(4-piperidin-1-ylmethyl-phenyl)-but-3-ynyl]-amine; dimethyl-[4-(4-piperidin-1-yl-but-1-ynyl)-benzyl]-amine; phenyl-[4-(4-piperidin-1-yl-but-1-ynyl)-benzyl]-amine; 1-[4-(3-aziridin-1-ylmethyl-phenyl)-but-3-ynyl]pyridine; 2-{1-[3-(4-piperidin-1-yl-but-1-ynyl)-benzyl]-piperidin-4-yloxy}-pyrimidine; {1-[3-(4-piperidin-1-yl-but-1-ynyl)-benzyl]-piperidin-4-yl}-pyridin-2-yl-amine; 4-[4-(3-morpholin-4-ylmethyl-phenyl)-but-3-ynyl]-morpholine; 4-[3-(4-thiomorpholin-4-yl-but-1-ynyl)-benzyl]-morpholine; 4-[3-(4-piperidin-1-yl-but-1-ynyl)-benzyl]-thiomorpholine; 4-[4-(3-thiomorpholin-4-ylmethyl-phenyl)-but-3-ynyl]-morpholine; 4-[3-(4-thiomorpholin-4-yl-but-1-ynyl)- benzyl]-thiomorpholine; 4-{4-[3-(4-methyl-piperazin-1-ylmethyl)-phenyl]-but-3-ynyl}-morpholine; 4-{4-[3-(4-methyl-piperazin-1-ylmethyl)-phenyl]-but-3-ynyl}-thiomorpholine; 1-methyl-4-[3-(4-piperidin-1-yl-but-1-ynyl)-benzyl]-piperazine; 1-[3-(4-piperidin-1-yl-but-1-ynyl)-benzyl]-piperidin-4-ol; 1-[3-(4-morpholin-4-yl-but-1-ynyl)-benzyl]-piperidin-4-ol; 1-[3-(4-thiomorpholin-4-yl-but-1-ynyl)-benzyl]-piperidin-4-ol; 1-{4-[3-methoxy-piperidin-1-ylmethyl)-phenyl]-but-3-ynyl}-piperidine; 4-{4-[3-(4-methoxy-piperidin-1-ylmethyl)-phenyl]-but-3-ynyl}-morpholine; and 4-{4-[3-(4-methoxy-piperidin-1-ylmethyl)-phenyl]-but-3-ynyl}-thiomorpholine.

Additional compounds include: 1-[4-(4-piperidin-1-ylmethyl-phenyl)-but-3-ynyl]-piperidine; 1-[3-(4-piperidin-1-yl-but-1-ynyl)-benzyl]-piperidine; 4-[3-(4-piperidin-1-yl-but-1-ynyl)-benzyl]-morpholine; 4-[3-(4-piperidin-1-yl-but-1-ynyl)-benzyl]-morpholine dihydrochloride; 1-[4-(4-pyrrolidin-1-yl-but-1-ynyl)-benzyl]-piperidine; 1-[4-(4-pyrrolidin-1-ylmethyl-phenyl)-but-3-ynyl]-piperidine; diethyl-[4-(4-piperidin-1-yl-but-1-ynyl)-benzyl]-amine; 1-[4-(4-piperidin-1-yl-but-1-ynyl)-benzyl]-piperidin4-ol; 2-(1-[4-(4-piperidin-1-yl-but-1-ynyl)-benzyl]-piperidin-2-yl)ethanol; 1-[4-(4-piperidin-1-yl-but-1-ynyl)-benzyl]-decahydro-quinoline; 1-[4-(4-piperidin-1-yl-but-1-ynyl)-benzyl]-piperidine4-carboxylic acid amide; 8-[4-(4-piperidin-1-yl-but-1-ynyl)-benzyl]-1,4-dioxa-8-aza-spiro[4.5]decane; 1-methyl4-[4-(4-piperidin-1-yl-but-1-ynyl)-benzyl]-piperazine; cyclohexyl-[4-(4-piperidin-1-yl-but-1-ynyl)-benzyl]-amine; indan-1-yl-[4-(4-piperidin-1-yl-but-1-ynyl)-benzyl]-amine; 1-[4-(4-piperidin-1-yl-but-1-ynyl)-benzyl]-piperazine; 1-isopropyl-4-[4-(4-piperidin-1-yl-but-1-ynyl)-benzyl]-piperazine; 1-phenyl-8-[3-(4-piperidin-1-yl-but-1-ynyl)-benzyl]-1,3,8-triaza-spiro[4.5]decan-4-one; 1-[3-(4-piperidin-1-yl-but-1-ynyl)-benzyl]-piperidine-4-carboxylic acid amide; 4-[3-(4-piperidin-1-yl-but-1-ynyl)-benzyl]-thiomorpholine; allyl-cyclopentyl-[3-(4-piperidin-1-yl-but-1-ynyl)-benzyl]-amine; 10-[3-(4-piperidin-1-yl-but-1-ynyl)-benzyl]-1,4,7-trioxa-10-aza-cyclododecane; 1-[4-(3-thiazolidin-3-ylmethyl-phenyl)-but-3-ynyl]-piperidine; [2-(1H-indol-3-yl)-ethyl]-methyl-[3-(4-piperidin-1-yl-but-1-ynyl)-benzyl]-amine; 1-{1-[3-(4-piperidin-1-yl-but-1-ynyl)-benzyl]-piperidin-4-yl}-1,3-dihydro-benzoimidazol-2-one; and 1-[4-(3-pyrrolidin-1-ylmethyl-phenyl)-but-3-ynyl]-piperidine.

More preferred compounds include: 4-[3-(4-piperidin-1-yl-but-1-ynyl)-benzyl]-morpholine and 4-[4-(4-piperidin-1-yl-but-1-ynyl)-benzyl]-morpholine; and particularly the former.

Additional examples of compounds include: 1-[3-(4-piperidin-1-yl-but-1-ynyl)-benzyl]-piperidine; 4-[3-(4-piperidin-1-yl-but-1-ynyl)-benzyl]-morpholine; 4-[3-(4-piperidin-1-yl-but-1-ynyl)-benzyl]-morpholine dihydrochloride; 1-phenyl-8-[3-(4-piperidin-1-yl-but-1-ynyl)-benzyl]-1,3,8-triaza-spiro[4.5]decan-4-one; 1-[3-(4-piperidin-1-yl-but-1-ynyl)-benzyl]-piperidine-3-carboxylic acid diethylamide; 1-[3-(4-piperidin-1-yl-but-1-ynyl)-benzyl]-1,2,3,4,5,6-hexahydro-[2,3']bipyridinyl; 1-[3-(4-piperidin-1-yl-but-1-ynyl)-benzyl]4-(3-trifluoromethyl-phenyl)-piperazine; 2-{4-[3-(4-piperidin-1-yl-but-1-ynyl)-benzyl]-piperazin-1-yl}-pyrimidine; 1-[3-piperidin-1-yl-but-1-ynyl)-benzyl]-piperidine-4-carboxylic acid amide; methyl-[3-(4-piperidin-1-yl-but-1-ynyl)-benzyl]-(2-pyridin-2-yl-ethyl)-amine; [2-(3,4-dimethoxy-phenyl)-ethyl]-methyl-[3-(4-piperidin-I -yl-but-1-ynyl)-benzyl]-amine; 4-[3-(4-piperidin-1-yl-but-1-ynyl)-benzyl]-thiomorpholine; allyl-cyclopentyl-[3-(4-piperidin-1-yl-but-1-ynyl)-benzyl]-amine; 10-[3-(4-piperidin-1-yl-but-1-ynyl)-benzyl]-1,4,7-trioxa-10-aza-cyclododecane; 1-[4-(3-thiazolidin-3-ylmethyl-phenyl)-but-3-ynyl]-piperidine; [2-(1H-indol-3-yl)-ethyl]-methyl-[3-(4-piperidin-1-yl-but-1-ynyl)-benzyl]-amine; 1-{1-[3-(4-piperidin-1-yl-but-1-ynyl)-benzyl]-piperidin-4-yl}-1,3-dihydro-benzoimidazol-2-one; phenyl-[3-(4-piperidin-1-yl-but-1-ynyl)-benzyl]-amine; 1-[4-(3-pyrrolidin-1-ylmethyl-phenyl)-but-3-ynyl]-piperidine; and 1-[3-(4-piperidin-1-yl-but-1-ynyl)-benzyl]-azacyclotridecane.

Further examples include: dimethyl-[4-(4-piperidin-1-ylmethyl-phenyl)-but-3-ynyl]-amine; dimethyl-[4-(4-piperidin-1-yl-but-1-ynyl)-benzyl]-amine; phenyl-[4-(4-piperidin-1-yl-but-1-ynyl)-benzyl]-amine; 1-[4-(3-aziridin-1-ylmethyl-phenyl)-but-3-ynyl]-piperidine; 2-{1-[3-(4-piperidin-1-yl-but-1-ynyl)-benzyl]-piperidin-4-yloxy}-pyrimidine; {1-[3-(4-piperidin-1-yl-but-1-ynyl)-benzyl]-piperidin-4-yl}-pyridin-2-yl-amine; 4-[4-(3-morpholin-4-ylmethyl-phenyl)-but-3-ynyl]-morpholine; 4-[3-(4-thiomorpholin-4-yl-but-1-ynyl)-benzyl]-morpholine; 4-[3-(4-piperidin-1-yl-but-1-ynyl)-benzyl]-thiomorpholine; 4-[4-(3-thiomorpholin-4-ylmethyl-phenyl)-but-3-ynyl]-morpholine; 4-[3-(4-thiomorpholin-4-yl-but-1-ynyl)-benzyl]-thiomorpholine; 4-{4-[3-(4-methyl-piperazin-1-ylmethyl)-phenyl]-but-3-ynyl}-morpholine; 4-{4-[3-(4-methyl-piperazin-1-ylmethyl)-phenyl]-but-3-ynyl}-thiomorpholine; 1-methyl-4-[3-(4-piperidin-1-yl-but-1-ynyl)-benzyl]-piperazine; 1-[3-(4-piperidin-1-yl-but-1-ynyl)-benzyl]-piperidin-4-ol; 1-[3-(4-morpholin-4-yl-but-1-ynyl)-benzyl]-piperidin-4-ol; 1-[3-(4-thiomorpholin-4-yl-but-1-ynyl)-benzyl]-piperidin-4-ol; 1-{4-[3-(4-methoxy-piperidin-1-ylmethyl)-phenyl]-but-3-ynyl}-piperidine; 4-{4-[3-(4-methoxy-piperidin-1-ylmethyl)-phenyl]-but-3-ynyl}-morpholine; and 4-{4-[3-(4-methoxy-piperidin-1-ylmethyl)-phenyl]-but-3-ynyl}-thiomorpholine.

The invention also provides compounds that are useful as synthetic intermediates of the compounds of the invention. Such compounds, which themselves may or may not have pharmaceutical activity, include those provided in the schemes and synthetic examples.

The invention also contemplates compounds isotopically-labelled to be detectable by positron emission tomography (PET) or single-photon emission computed tomography (SPECT) useful for studying $H_3$-mediated disorders.

During any of the processes for preparation of the compounds of the present invention, it may be necessary and/or desirable to protect sensitive or reactive groups on any of the molecules concerned. In addition, compounds of the invention may be modified by using protecting groups; such compounds, precursors, or prodrugs are also within the scope of the invention. This may be achieved by means of conventional protecting groups, such as those described in "Protective Groups in Organic Chemistry", ed. J. F. W. McOmie, Plenum Press, 1973; and T. W. Greene & P. G. M. Wuts, "Protective Groups in Organic Synthesis", $3^{rd}$ ed., John Wiley & Sons, 1999. The protecting groups may be removed at a convenient subsequent stage using methods known from the art.

Hydroxyl Protecting Groups

Protection for the hydroxyl group includes methyl ethers, substituted methyl ethers, substituted ethyl ethers, substitute benzyl ethers, and silyl ethers.

Substituted Methyl Ethers

Examples of substituted methyl ethers include methyoxymethyl, methylthiomethyl, t-butylthiomethyl, (phenyldimethylsilyl)methoxymethyl, benzyloxymethyl, p-methoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxido, 1-[(2-chloro4-methyl)phenyl]4-methoxypiperidin-4-yl, 1,4-dioxan-2-yl, tetrahydrofuranyl, tetrahydrothiofuranyl and 2,3,3a,4,5,6,7,7a-octahydro-7,8,8-trimethyl-4,7-methanobenzofuran-2-yl.

Substituted Ethyl Ethers

Examples of substituted ethyl ethers include 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, and benzyl.

Substituted Benzyl Ethers

Examples of substituted benzyl ethers include p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p, p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(Imidazol-1-ylmethyl)bis(4', 4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, and benzisothiazolyl S,S-dioxido.

Silyl Ethers

Examples of silyl ethers include trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, and t-butylmethoxyphenylsilyl.

Esters

In addition to ethers, a hydroxyl group may be protected as an ester. Examples of esters include formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate(levulinate), 4,4-(ethylenedithio)pentanoate, pivaloate, adamantoate, crotonate, 4-methoxycrotonate, benzoate, p-phenylbenzoate, 2,4,6-trimethylbenzoate(mesitoate)

Carbonates

Examples of carbonates include methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, and methyl dithiocarbonate.

Assisted Cleavage

Examples of assisted cleavage include 2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, and 2-(methylthiomethoxymethyl)benzoate.

Miscellaneous Esters

Examples of miscellaneous esters include 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate (tigloate), o-(methoxycarbonyl)benzoate, p-P-benzoate, α-naphthoate, nitrate, alkyl N,N,N',N'-tetramethylphosphorodiamidate, N-phenylcarbamate, borate, dimethylphosphinothioyl, and 2,4-dinitrophenylsulfonate Sulfonates Examples of sulfonates include sulfate, methanesulfonate (mesylate), benzylsulfonate, and tosylate.

Protection for 1,2- and 1,3-Diols

Cyclic Acetals and Ketals

Examples of cyclic acetals and ketals include methylene, ethylidene, 1-t-butylethylidene, 1-phenylethylidene, (4-methoxyphenyl)ethylidene, 2,2,2-trichloroethylidene, acetonide (isopropylidene), cyclopentylidene, cyclohexylidene, cycloheptylidene, benzylidene, p-methoxybenzylidene, 2,4-dimethoxybenzylidene, 3,4-dimethoxybenzylidene, and 2-nitrobenzylidene.

Cyclic Ortho Esters

Examples of cyclic ortho esters include methoxymethylene, ethoxymethylene, dimethoxymethylene, 1-methoxyethylidene, 1-ethoxyethylidine, 1,2-dimethoxyethylidene, α-methoxybenzylidene, 1-(N,N-dimethylamino)ethylidene derivative, α-(N,N-dimethylamino)benzylidene derivative, and 2-oxacyclopentylidene.

Silyl Derivatives

Examples of silyl derivatives include di-t-butylsilylene group, and 1,3-(1,1,3,3-tetraisopropyldisiloxanylidene) derivative.

Amino Protecting Groups

Protection for the amino group includes carbamates, amides, and special —NH protective groups.

Examples of carbamates include methyl and ethyl carbamates, substituted ethyl carbamates, assisted cleavage carbamates, photolytic cleavage carbamates, urea-type derivatives, and miscellaneous carbamates.

Carbamates

Examples of methyl and ethyl carbamates include methyl and ethyl, 9-fluorenylmethyl, 9-(2-sulfo)fluorenylmethyl, 9-(2,7-dibromo)fluorenylmethyl, 2,7-di-t-butyl-[9-(10,10-dioxo-10,10,10,10-tetrahydrothioxanthyl)]methyl, and 4-methoxyphenacyl.

Substituted Ethyl

Examples of substituted ethyl carbamates include 2,2,2-trichloroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl,-1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl) ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl and diphenylmethyl.

Assisted Cleavage

Examples of assisted cleavage include 2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-chloro-p-acyloxybenzyl, p-(dihydroxyboryl) benzyl, 5-benzisoxazolylmethyl, and 2-(trifluoromethyl)-6-chromonylmethyl.

Photolytic Cleavage

Examples of photolytic cleavage include m-nitrophenyl, 3,5-dimethoxybenzyl, o-nitrobenzyl, 3,4-dimethoxy-6-nitrobenzyl, and phenyl(o-nitrophenyl)methyl.

Urea-Type Derivatives

Examples of urea-type derivatives include phenothiazinyl-(10)-carbonyl derivative, N'-p-toluenesulfonylaminocarbonyl, and N'-phenylaminothiocarbonyl.

Miscellaneous Carbamates

Examples of miscellaneous carbamates include t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido) benzyl, 1,1-dimethyl-3-(N,N-dimethylcarboxamido)propyl, 1,1-dimethylpropynyl, di(2-pyridyl)methyl, 2-furanylmethyl, 2-iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(3,5-dimethoxyphenyl) ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, and 2,4,6-trimethylbenzyl.

Examples of Amides Include:

Amides

N-formyl, N-acetyl, N-chloroacetyl, N-trichloroacetyl, N-trifluoroacetyl, N-phenylacetyl, N-3-phenylpropionyl, N-picolinoyl, N-3-pyridylcarboxamide, N-benzoylphenylalanyl derivative, N-benzoyl, N-p-phenylbenzoyl.

Assisted Cleavage

N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl) propionyl, N-2-methyl-2-(o-nitrophenoxy)propionyl, N-2-methyl-2-(o-phenylazophenoxy)propionyl, N4-chlorobutyryl, N-3-methyl-3-nitrobutyryl, N-o-nitrocinnamoyl, N-acetylmethionine derivative, N-o-nitrobenzoyl, N-o-(benzoyloxymethyl)benzoyl, and 4,5-diphenyl-3-oxazolin-2-one.

Cyclic Imide Derivatives

N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3,5-triazacyclohexan-2-one, and 1-substituted 3,5-dinitro-4-pyridonyl.

Special—NH Protective Groups

Examples of special NH protective groups include:

N-Alkyl and N-Aryl Amines

N-methyl, N-allyl, N-[2-(trimethylsilyl)ethoxy]methyl, N-3-acetoxypropyl, N-(1-isopropyl-4-nitro-2-oxo-3-pyrrolin-3-yl), quaternary ammonium salts, N-benzyl, N4-methoxybenzyl, N-di(4-methoxyphenyl)methyl, N-5-dibenzosuberyl, N-triphenylmethyl, N-(4-methoxyphenyl) diphenylmethyl, N-9-phenylfluorenyl, N-2,7-dichloro-9-fluorenylmethylene, N-ferrocenylmethyl, and N-2-picolylamine N'-oxide.

Imine Derivatives

N-1,1-dimethylthiomethylene, N-benzylidene, N-p-methoxybenzylidene, N-diphenylmethylene, N-[(2-pyridyl) mesityl]methylene, and N-(N',N'-dimethylaminomethylene).

Protection for the Carbonyl Group

Acyclic Acetals and Ketals

Examples of acyclic acetals and ketals include dimethyl, bis(2,2,2-trichloroethyl), dibenzyl, bis(2-nitrobenzyl) and diacetyl.

Cyclic Acetals and Ketals

Examples of cyclic acetals and ketals include 1,3-dioxanes, 5-methylene-1,3-dioxane, 5,5-dibromo-1,3-dioxane, 5-(2-pyridyl)-1,3-dioxane, 1,3-dioxanes, 4-bromomethyl-1,3-dioxolane, 4-(3-butenyl)-1,3-dioxolane, 4-phenyl-1,3-dioxolane, 4-(2-nitrophenyl)-1,3-dioxolane, 4,5-dimethoxymethyl-1,3-dioxolane, O,O'-phenylenedioxy and 1,5-dihydro-3H-2,4-benzodioxepin.

Acyclic Dithio Acetals and Ketals

Examples of acyclic dithio acetals and ketals include S,S'-dimethyl, S,S'-diethyl, S,S'-dipropyl, S,S'-dibutyl, S,S'-dipentyl, S,S'-diphenyl, S,S'-dibenzyl and S,S'-diacetyl.

Cyclic Dithio Acetals and Ketals

Examples of cyclic dithio acetals and ketals include 1,3-dithiane, 1,3-dithiolane and 1,5-dihydro-3H-2,4-benzodithiepin.

Acyclic Monothio Acetals and Ketals

Examples of acyclic monothio acetals and ketals include O-trimethylsilyl-S-alkyl, O-methyl-S-alkyl or —S-phenyl and O-methyl-S-2-(methylthio)ethyl.

Cyclic Monothio Acetals and Ketals

Examples of cyclic monothio acetals and ketals include 1,3-oxathiolanes.

Miscellaneous Derivatives

O-Substituted Cyanohydrins

Examples of O-substituted cyanohydrins include O-acetyl, O-trimethylsilyl, O-1-ethoxyethyl and O-tetrahydropyranyl.

Substituted Hydrazones

Examples of substituted hydrazones include N,N-dimethyl and 2,4-dinitrophenyl.

Oxime Derivatives

Examples of oxime derivatives include O-methyl, O-benzyl and O-phenylthiomethyl.

Imines

Substituted Methylene Derivatives, Cyclic Derivatives

Examples of substituted methylene and cyclic derivatives include oxazolidines, 1-methyl-2-(1'-hydroxyalkyl) imidazoles, N,N'-dimethylimidazolidines, 2,3-dihydro-1,3-benzothiazoles, diethylamine adducts, and methylaluminum bis(2,6-di-t-butyl4-methylphenoxide)(MAD)complex.

Monoprotection of Dicarbonyl Compounds

Selective Protection of α- and β-Diketones

Examples of selective protection of α- and β-diketones include enamines, enol acetates, enol ethers, methyl, ethyl, i-butyl, piperidinyl, morpholinyl, 4-methyl-1,3-dioxolanyl, pyrrolidinyl, benzyl, S-butyl, and trimethylsilyl.

Cyclic Ketals, Monothio and Dithio Ketals

Examples of cyclic ketals, monothio and dithio ketals include bismethylenedioxy derivatives and tetramethylbis-methylenedioxy derivatives.

Protection for the Carboxyl Group

Esters

Substituted Methyl Esters

Examples of substituted methyl esters include 9-fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, phenacyl, p-bromophenacyl, α-methylphenacyl, p-methoxyphenacyl, carboxamidomethyl, and N-phthalimidomethyl.

2-Substituted Ethyl Esters

Examples of 2-substituted ethyl esters include 2,2,2-trichloroethyl, 2-haloethyl, ω-chloroalkyl, 2-(trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(2'-pyridyl)ethyl, 2-(diphenylphosphino)ethyl, 1-methyl-1-phenylethyl, t-butyl, cyclopentyl, cyclohexyl, allyl, 3-buten-1-yl, 4-(trimethylsilyl)-2-buten-1-yl, cinnamyl, α-methylcinnamyl, phenyl, p-(methylmercapto)phenyl and benzyl.

Substituted Benzyl Esters

Examples of substituted benzyl esters include triphenylmethyl, diphenylmethyl, bis(o-nitrophenyl)methyl, 9-anthrylmethyl, 2-(9,10-dioxo)anthrylmethyl, 5-dibenzosuberyl, 1-pyrenylmethyl, 2-(trifluoromethyl)-6-chromylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, piperonyl, 4-picolyl and p-P-benzyl.

Silyl Esters

Examples of silyl esters include trimethylsilyl, triethylsilyl, t-butyldimethylsilyl, i-propyldimethylsilyl, phenyldimethylsilyl and di-t-butylmethylsilyl.

Activated Esters

Examples of activated esters include thiols.

Miscellaneous Derivatives

Examples of miscellaneous derivatives include oxazoles, 2-alkyl-1,3-oxazolines, 4-alkyl-5-oxo-1,3-oxazolidines, 5-alkyl-4-oxo-1,3-dioxolanes, ortho esters, phenyl group and pentaaminocobalt(III) complex.

Stannyl Esters

Examples of stannyl esters include triethylstannyl and tri-n-butylstannyl.

Amides and Hydrazides

Amides

Examples of amides include N,N-dimethyl, pyrrolidinyl, piperidinyl, 5,6-dihydrophenanthridinyl, o-nitroanilides, N-7-nitroindolyl, N-8-Nitro-1,2,3,4-tetrahydroquinolyl, and p-P-benzenesulfonamides.

Hydrazides

Examples of hydrazides include N-phenyl and N,N'-diisopropyl.

The compounds of the invention can be prepared according to the methods described in the next section.

C. Synthesis

The compounds of the invention can be prepared according to traditional synthetic organic methods and matrix or combinatorial chemistry methods, as shown in Schemes 1–5 below and in Examples 1–76. A person of ordinary skill will be aware of variations and adaptations of the schemes and examples provided to achieve the compounds of the invention.

One skilled in the art will recognize that synthesis of the compounds of the present invention may be effected by purchasing intermediate or protected intermediate compounds described in any of the Schemes disclosed herein. Throughout the schemes when the reacting functionality is located at $R^3$, one skilled in the art will recognize that the choice of $R^3$ is illustrative only and that the reacting functionality could also be located at $R^4$ and $R^5$ also.

One skilled in the art will further recognize that during any of the processes for preparation of the compounds of the present invention, it may be necessary and/or desirable to protect sensitive or reactive groups on any of the molecules concerned. This may be achieved by means of conventional protecting groups, such as those described in "Protective Groups in Organic Chemistry", ed. J. F. W. McOmie, Plenum Press, 1973; and T. W. Greene & P. G. M. Wuts, "Protective Groups in Organic Synthesis", John Wiley & Sons, 1991. The protecting groups may be removed at a convenient subsequent stage using methods known from the art.

Throughout the schemes when the reacting functionality is located at $R^5$, one skilled in the art will recognize that the choice of $R^5$ is illustrative only and that the reacting functionality could also be located at $R^3$ and/or $R^4$.

Compounds of formula (V) may be prepared according to the processes outlined in Scheme 1.

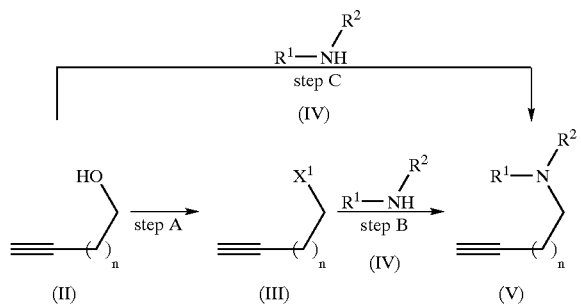

Scheme 1.

A compound of formula (V) is prepared as outlined in Scheme 1 from a compound of formula (II). A compound of formula (II) is reacted with a reagent capable of converting a hydroxyl function into a leaving group $X^1$ under hydroxyl activation conditions. In a preferred embodiment, leaving group $X^1$ is a sulfonate ester, obtained by reacting a compound of formula (III) with an alkyl or arylsulfonyl chloride in a solvent such as benzene, DCM, DCE, THF, hexane, or pentane in the presence of a base such as pyridine or TEA at temperature from –78° C. to 50° C. In a particularly preferred embodiment, a compound of formula (II) is reacted with p-toluenesulfonyl chloride or methanesulfonyl chloride in DCM in the presence of TEA at a temperature between 0° C. and room temperature. A compound of formula (V) is obtained from a compound of formula (III) by reacting a compound of formula (IV) with a compound of formula (III) under nucleophilic displacement conditions, either neat or in a solvent such as methanol, ethanol, propanol, n-butanol, DMF, or DME in the presence or absence of a base such as sodium carbonate, potassium carbonate, cesium carbonate, triethylamine, or tetramethylguanidine at a temperature from 0° C. to 100° C. One skilled in the art will recognize that the use of water as a cosolvent may increase the rate and reduce by-product formation in these reactions. In a preferred embodiment the solvent is water, ethanol, or a mixture of water and ethanol or propanol, the base is sodium or potassium carbonate or absent, and the temperature is room temperature to 80° C. In a particularly preferred embodiment, the solvent is ethanol, no exogenous base is used, and the temperature is 0° C. to room temperature. A compound of formula (V) may also be obtained from a compound of formula (II) by reaction of a compound of formula (IV) in the presence of a trialkylphosphonium halide such as (cyanomethyl)trimethylphosphonium iodide and a base such as DIPEA in a solvent such as propionitrile at 90° C.

Compounds of formula (I) may be prepared according to the processes outlined in Scheme 2.

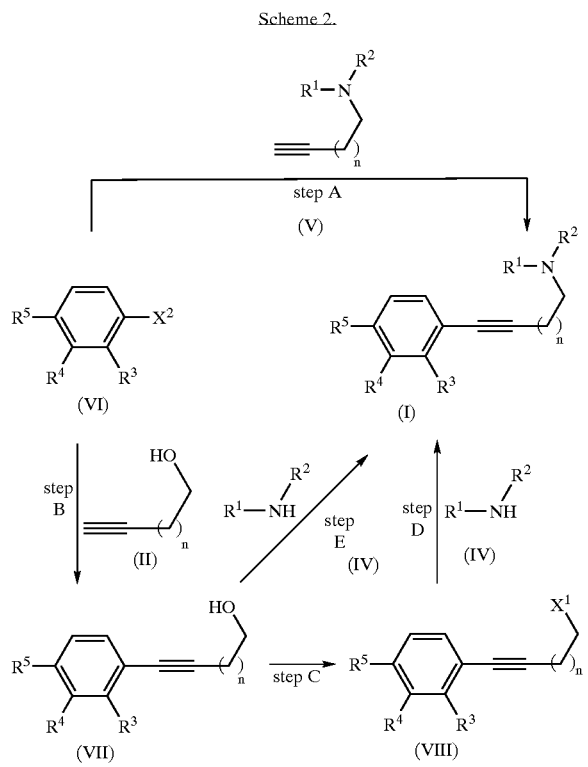

A compound of formula (I) is prepared from a compound of formula (VI) as shown in Scheme 2. A compound of formula (VI), in which the group $X^2$ denotes a leaving group such as trifluoromethanesulfonate, iodide, bromide, or chloride, is reacted with a compound of formula (II) under Sonogashira conditions in the presence of a palladium-containing entity such as palladium on carbon, $Pd(PPh_3)_2Cl_2$, $Pd_2(dba)_3$, $Pd_2(dba)_3 \cdot CHCl_3$, $Pd(P^tBu_3)_2$, $Pd_2(dba)_3 \cdot CHCl_3/Pd(P^tBu_3)_2$, $Pd(OAc)_2$, $Pd(PhCN)_2Cl_2$, and $PdCl_2$ and a base such as triethylamine, DIEA, di-iso-propylamine, sodium carbonate, potassium carbonate, or cesium carbonate in a solvent such as THF, DME, dioxane, DCE, DCM, toluene, and acetonitrile at a temperature from 0° C. to 100° C. One skilled in the art will recognize that the use of substoichiometric quantities of a copper salt such as CuI or $CuBrMe_2S$ and phosphine ligands such as $PPh_3$ or $P(^tBu)_3$ may be necessary. One skilled in the art will further realize that the use of water as a cosolvent may accelerate the reaction and prevent the formation of byproducts. In a preferred embodiment, the palladium source is $Pd_2(dba)_3 \cdot CHCl_3/Pd(P^tBu_3)_2$, $Pd(PPh_3)_2Cl_2$, or palladium on carbon, the base is triethylamine or potassium carbonate, the solvent is THF, or a mixture of DME and water, and the temperature is between room temperature and 80° C. In a particularly preferred embodiment, the palladium source is $Pd(PPh_3)_2Cl_2$, the base is triethylamine, the solvent is THF, a catalytic quantity of CuI or $CuBrMe_2S$ is used, and the reaction temperature is room temperature to reflux temperature. A compound of formula (I) is obtained from a compound of formula (VII) in analogy with Scheme 1, steps A and B, or by analogy with Scheme 1 step C. A compound of formula (I) may also be obtained directly from a compound of formula (VI) by reaction with a compound of formula (V) under Sonogashira conditions.

Compounds of formula (XII) may be prepared according to the processes outlined in Scheme 3.

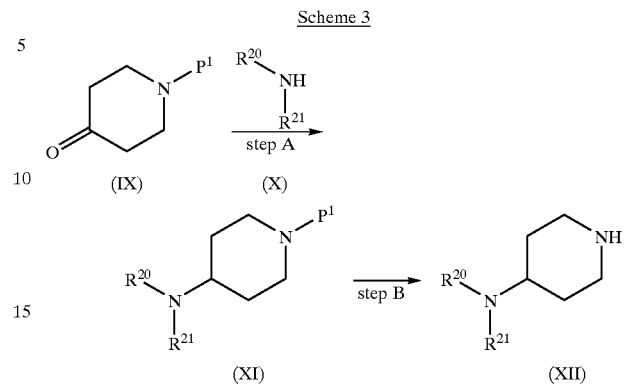

A compound of formula (XII) is prepared as outlined in Scheme 3 from a compound of formula (IX). One skilled in the art will be capable of selecting a suitable protecting group $P^1$ for the compound of formula (IX). A compound of formula (IX) is reacted with a compound of formula (X) under reductive amination conditions in the presence of a reducing agent such as $NaBH(OAc)_3$ in a solvent such as DCE or THF at a temperature from 0° C. to 80° C. One skilled in the art will recognize that the addition of an acid such as acetic acid may accelerate the reaction and decrease byproduct formation. In a particularly preferred embodiment, a compound of formula (IX) is reacted with a compound of formula (X) in the presence of $NaBH(OAc)_3$ and acetic acid in DCE at room temperature. A compound of formula (XII) is obtained from a compound of formula (XI) by removal of the protecting $P^1$ under conditions familiar to one skilled in the art.

Compounds of formula (XVI) may be prepared according to the processes outlined in Scheme 4.

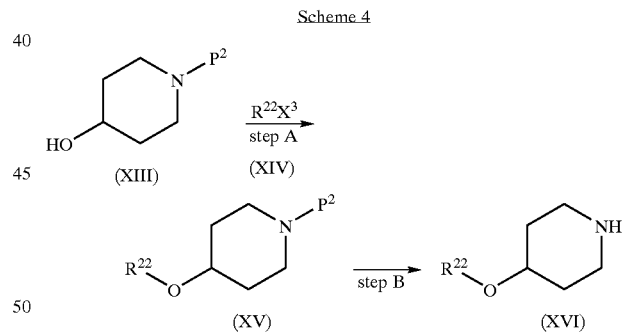

A compound of formula (XVI) is prepared as outlined in Scheme 4 from a compound of formula (XIII). One skilled in the art will be capable of selecting a suitable protecting group $P^2$ for the compound of formula (XIII). A compound of formula (XIII) is reacted with a compound of formula (XIV), where $X^3$ is a leaving group such a halogen or an activated ester, in the presence of a base, such as sodium hydride, potassium hydride, sodium hydroxide, potassium hydroxide, DBU, triethylamine, or butyllithium in a solvent such as DMF, THF, toluene, DMAC, or acetonitrile, at a temperature from room temperature to 140° C. Alternatively, a compound of formula (XIII) is reacted with a compound of formula (XIV), where $X^3$ is hydroxyl and $R^{22}$ is an aromatic group, under Mitsunobu conditions. A compound of formula (XVI) is obtained from a compound of formula (XV) by removal of the protecting $P^2$ under conditions familiar to one skilled in the art.

Compounds of formula (XXVI) may be prepared according to the processes outlined in Scheme 5.

conditions, as described in Scheme 2, step A. Alternatively, a compound of formula (XXVII) is obtained by reacting a compound of formula (XXIII) with a compound of formula (V) under Sonogashira conditions, as described in Scheme 2,

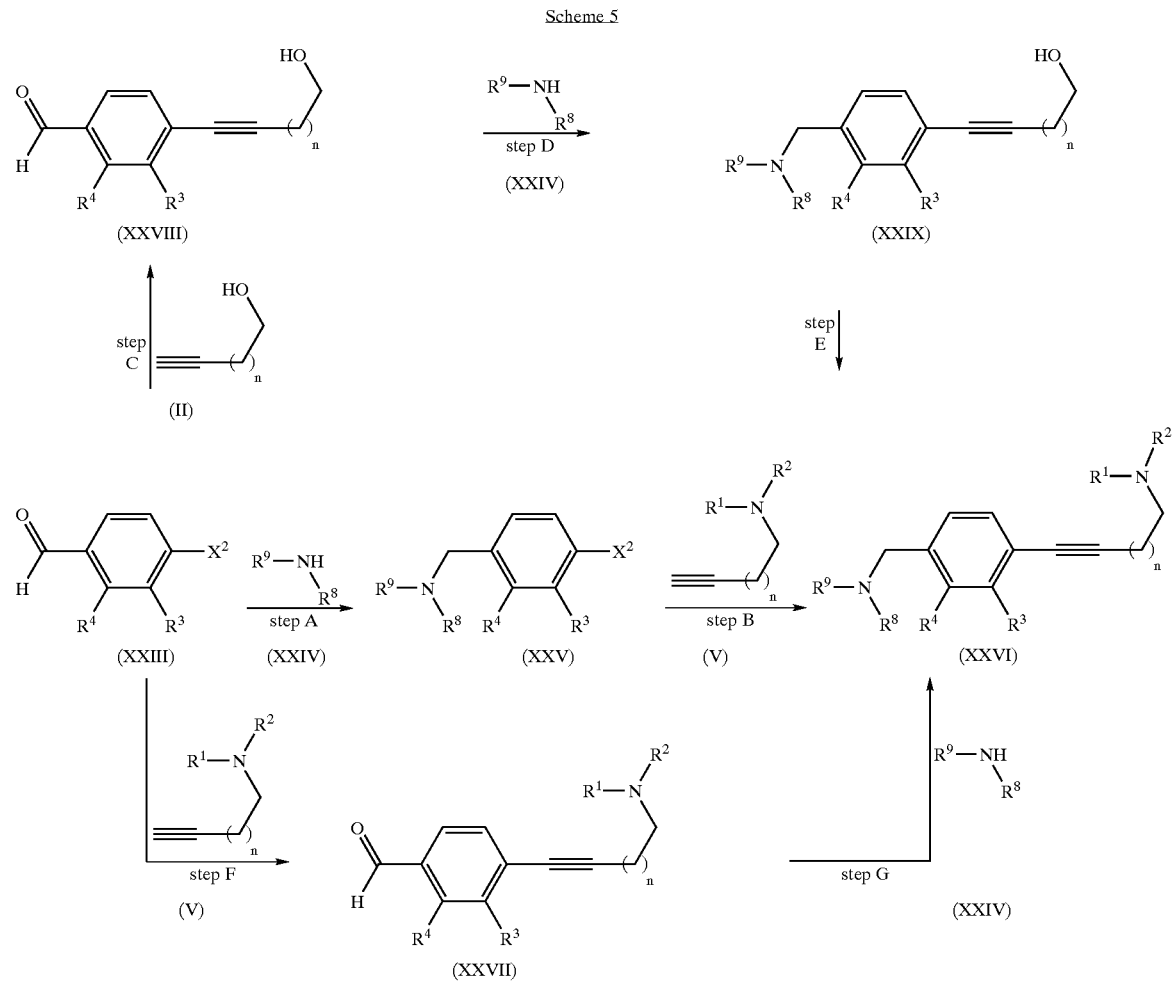

Scheme 5

A compound of formula (XXVI) is prepared from a compound of formula (XXIII) as outlined in Scheme 5. The group $X^2$ in the compound of formula (XXIII) denotes a leaving group, as defined in Scheme 2. A compound of formula (XXVIII) is obtained by reacting a compound of formula (XXIII) with a compound of formula (II) under Sonogashira conditions, as outlined in Scheme 2, step A. A compound of formula (XXIX) is obtained by reacting a compound of formula (XXVIII) with a compound of formula (XXIV) under reductive amination conditions as outlined in Scheme 3, step A. One skilled in the art will recognize that a substituted or unsubstituted nonaromatic heterocycle containing secondary amine functionality, such as a compound of formula (A) may be used in place of the compound of formula (XXIV). A compound of formula (XXVI) is obtained by reacting a compound of formula (XXIX) under the conditions described in Scheme 1, step C, or Scheme 1, steps A and B. Alternatively, a compound of formula (XXV) is obtained by reacting a compound of formula (XXIII) under reductive amination conditions, as described in Scheme 3, step A. A compound of formula (XXVI) is obtained by reacting a compound of formula (XXV) with a compound of formula (V) under Sonogashira step A. A compound of formula (XXVI) is obtained by reacting a compound of formula (XXVII) with a compound of formula (XXIV) under reductive amination conditions, as described in Scheme 3, step A.

D. Formulation, Administration, and Therapy

The disclosed compounds, alone or in combination (with, for example, a histamine $H_1$ receptor antagonist), are useful for treating or preventing neurologic disorders including sleep/wake and arousal/vigilance disorders (e.g. insomnia and jet lag), attention deficit hyperactivity disorders (ADHD), learning and memory disorders, cognitive dysfunction, migraine, neurogenic inflammation, dementia, mild cognitive impairment (pre-dementia), Alzheimer's disease, epilepsy, narcolepsy, eating disorders, obesity, motion sickness, vertigo, schizophrenia, substance abuse, bipolar disorders, manic disorders and depression, as well as other histamine $H_3$ receptor mediated disorders such as upper airway allergic response, asthma, itch, nasal congestion and allergic rhinitis in a subject in need thereof.

1. Formulation and Administration

The compounds or compositions of the invention may be formulated and administered to a subject by any conventional route of administration, including, but not limited to, intravenous, oral, subcutaneous, intramuscular, intradermal and parenteral administration. The quantity of the compound which is effective for treating each condition may vary, and can be determined by one of ordinary skill in the art.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali ml salts, e.g., sodium or potassium salts; alkaline earth ml salts, e.g., calcium or magnesium salts; and salts formed with suitable organic ligands, e.g., quaternary ammonium salts.

Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985. In addition to salts, the invention provides the esters, amides, and other protected or derivatized forms of the described compounds.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The present invention also provides pharmaceutical compositions comprising one or more compounds of this invention in association with a pharmaceutically acceptable carrier and optionally additional pharmaceutical agents such as $H_1$ antagonists or SSRIs. Preferably these compositions are in unit dosage forms such as pills, tablets, caplets, capsules (each including immediate release, timed release and sustained release formulations), powders, granules, sterile parenteral solutions or suspensions (including syrups and emulsions), metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 5 to about 1000 mg of the active ingredient of the present invention. Examples include 5 mg, 7 mg, 10 mg, 15 mg, 20 mg, 35 mg, 50 mg, 75 mg, 100 mg, 120 mg, 150 mg, and so on. The tablets or pills of the disclosed compositions can be coated or otherwise compounded to provide a dosage form affording the advantage of prolonged action. For example, the tablet or pill can comprise an inner dosage and an outer dosage component, the latter being in the form of an envelope over the former. The two components can be septed by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the compounds and compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyric acid, polyesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of ADHD is required.

The daily dosage of the products may be varied over a wide range from 1 to 1,000 mg per adult human per day. For oral administration, the compositions are preferably provided in the form of tablets containing 1.0, 5.0, 10.0, 15.0, 25.0, 50.0, 100, 250 and 500 milligrams of the active ingredient for the symptomatic adjustment of the dosage to the subject to be treated. An effective amount of the drug is ordinarily supplied at a dosage level of from about 0.01 mg/kg to about 20 mg/kg of body weight per day. Preferably, the range is from about 0.02 mg/kg to about 10 mg/kg of body weight per day, and especially from about 0.05 mg/kg to about 10 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

2. Combination Therapy

The disclosed compounds are useful in combination with other therapeutic agents, including HI receptor antagonists, $H_2$ receptor antagonists, and neurotransmitter modulators such as SSRIs and non-selective serotonin re-uptake inhibitors (NSSRIs).

Methods are known in the art for determining effective doses for therapeutic and prophylactic purposes for the disclosed pharmaceutical compositions or the disclosed drug combinations, whether or not formulated in the same composition. For therapeutic purposes, the term "jointly effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "jointly effective amount" refers to that amount of each active compound or pharmaceutical agent, alone or in combination, that inhibits in a subject the onset or progression of a disorder as being sought by a researcher, veterinarian, medical doctor or other clinician, the delaying of which disorder is mediated, at least in part, by the modulation of one or more histamine receptors. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both drugs are administered in an amount that is sub-therapeutic or sub-prophylactic if administered alone, but are therapeutic or prophylactic when administered together.

Combinations of three or more drugs are analogously possible. Methods of combination therapy include co-administration of a single formulation containing all active agents; essentially contemporaneous administration of more than one formulation; and administration of two or more active agents separately formulated.

E. EXAMPLES

Example 1

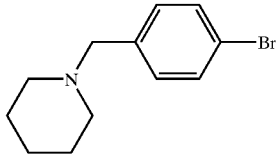

1-(4-Bromo-benzyl)-piperidine

A solution of 4-bromobenzaldehyde (5 g), piperidine (2.9 mL), and acetic acid (1.5 mL) in DCE (65 mL) was treated with sodium triacetoxyborohydride (6.9 g). After 27 h, the resulting mixture was treated with saturated aqueous sodium bicarbonate (50 mL), and extracted with DCM (2×50 mL). The combined organic phases were dried (magnesium sulfate) and evaporated. Kugelrohr distillation of the residue (160° C., 5 mm Hg) gave the title compound as a pale yellow oil (5.9 g).

Example 2

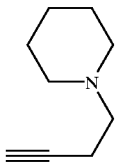

1-But-3-ynyl-piperidine

A solution of toluene-4-sulfonic acid but-3-ynyl ester (45.0 g) and piperidine (40 mL) in ethanol (70 mL) was treated a solution of potassium carbonate (27.8 g) in water (70 mL). The mixture was heated to 80° C. for 2 h, cooled to RT, and extracted with DCM (3×100 mL). The combined organic phases were dried (magnesium sulfate), and evaporated. Distillation of the residue (110° C., 30 mm Hg) gave the title compound as a colorless oil (17.3 g).

Example 3

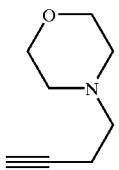

4-But-3-ynyl-morpholine

May be prepared analogously to Example 2 using morpholine.

Example 4

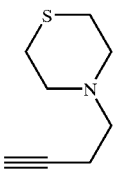

4-But-3-ynyl-thiomorpholine

May be prepared analogously to Example 2 using thiomorpholine.

Example 5

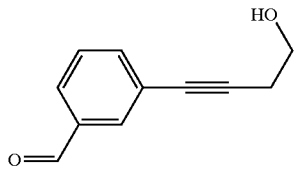

3-(4-Hydroxy-but-1-ynyl)-benzaldehyde

A 1-L, 3-necked round-bottom flask was equipped with a magnetic stirring bar, a condenser with a nitrogen inlet, and two stoppers. The vessel was charged with 3-bromobenzaldehyde (18.5 g), 3-butyn-1-ol (10.5 g), triethylamine (100 mL), and THF (100 mL). To this mixture was then added PdCl$_2$(PPh$_3$)$_2$ (1.4 g) and CuBrMe$_2$S (0.405 g). The reaction mixture was heated to reflux using a heating mantle. After 4 h when TLC showed complete consumption of the bromide, the mixture was allowed to cool to room temperature, transferred to a 1-L round-bottom flask and concentrated under reduced pressure. The residue was dissolved in 250 mL of ethyl acetate. The solution was washed with water and brine, dried over MgSO$_4$, and filtered. The solvents were removed from the filtrate under reduced pressure to obtain the title compound as pale yellow oil (16.8 g).

Example 6

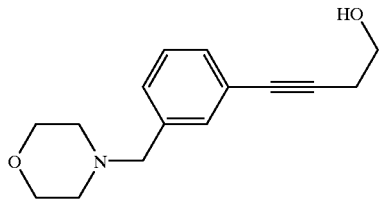

4-(3-Morpholin-4-ylmethyl-phenyl)-but-3-yn-1-ol

A 1-L, 3-necked round-bottom flask was equipped with a mechanical stirrer, a rubber septum with a nitrogen inlet and a stopper. The flask was charged with the product of Example 5 (14.6 g) and dichloromethane (250 mL). Morpholine (8.85 mL) was added, and then to this well-stirred reaction mixture was added sodium triacetoxyborohydride (32 g) in 4 equal portions. After the addition, the reaction mixture was stirred at room temperature overnight. Aqueous NaOH (10% w/v, 75 mL) was added, and the reaction mixture was transferred to a 1-L separatory funnel, to which water(100 mL) was then added. After separation of the layers, the aqueous phase was extracted once with dichloromethane (100 mL). The combined organic extracts were washed with brine (30 mL), dried over MgSO$_4$, and filtered. The solvents were removed from the filtrate under reduced pressure to yield the product as yellow oil. The crude product was purified by filtration through a pad of silica gel (ethyl acetate/hexanes; 7:3) to obtain the title compound as a pale yellow oil (13.7 g).

Example 7

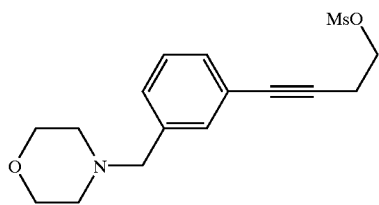

Methanesulfonic acid 4-(3-morpholin-4-ylmethyl-phenyl)-but-3-ynyl ester

A 500-mL 1-necked round-bottom flask was equipped with a magnetic stirring bar and rubber septum with a nitrogen inlet. The vessel was charged with the product of Example 6 (13.6 g), dichloromethane (100 mL) and triethylamine (8.43 mL). The reaction mixture was cooled to 0° C. in an ice bath, and a solution of methanesulfonyl chloride (6.93 g) in dichloromethane (10 mL) was added in drops over 30 min. The cooling was removed and the reaction mixture was allowed to warm up to room temperature. After 1 h when TLC indicated complete conversion, 50 mL ice water was added, and the reaction mixture was transferred to a 500-mL separatory funnel. The organic extract was separated and washed with aqueous NaHCO$_3$, brine, and dried over MgSO$_4$. After filtration, the solvents were evaporated under reduced pressure (rotary evaporator, 30° C.) to obtain the title compound as pale yellow gum (17.5 g).

Example 8

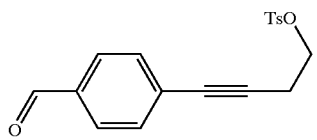

Toluene-4-sulfonic acid 4-(4-formyl-phenyl)-but-3-ynyl ester

A mixture of 4-bromobenzaldehyde (25.0 g), potassium carbonate (46.6 g), copper(I) iodide (1.0 g), triphenylphosphine (2.8 g), 10% palladium on carbon (288 mg) in water (250 mL) and DME (250 mL) was stirred at room temperature for 30 min, and 3-butyn-1-ol (25 mL) was added. The resulting mixture was heated at 90° C. for 16 h, cooled to room temperature, and filtered through a pad of Celite. The pad was washed with DCM (3×50 mL), and the filtrate was diluted with water (100 mL). The aqueous phase was extracted with ethyl acetate (2×400 mL), and the combined organic phases were washed with water (100 mL) and brine (100 mL), dried (magnesium sulfate), and concentrated under reduced pressure. The residue was azeotroped with toluene (2×100 mL) to give a brown solid (2.1 g). To a solution of this solid and triethylamine (7.1 mL) in DCM (100 mL) was added p-toluene sulfonyl chloride at 0° C. The resulting mixture was warmed to room temperature over a period of 2.5 h, diluted with water (10 mL), and extracted with DCM (2×300 mL). The combined organic phases were washed with water (2×40 mL) and brine (40 mL), and then dried (magnesium sulfate) and concentrated under reduced pressure. Chromatography of the residue (10–20% ethylacetate/hexane) gave the title compound as a yellow oil (6.7 g).

Example 9

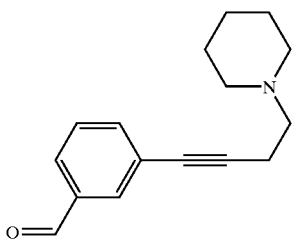

3-(4-Piperidin-1-yl-but-1-ynyl)-benzaldehyde

A mixture of 3-bromobenzaldehyde (0.58 mL), potassium carbonate (1.73 g), copper(I) iodide (38 mg), triphenylphosphine (105 mg), 10% palladium on carbon (220 mg) in water (10 mL) and DME (5 mL) was stirred at room temperature for 20 min, and treated with a solution of the product of Example 2 (1.7 g) in DME (5 mL). The resulting mixture was heated at 80° C. for 16 h, cooled to room temperature, and filtered through a pad of Celite. The pad was washed with DCM (5×20 mL), and the filtrate was diluted with water (30 mL). The aqueous phase was extracted with DCM (2×30 mL), and the combined organic phases were dried (magnesium sulfate) and concentrated under reduced pressure. Chromatography of the residue (0–3% 2 M methanolic ammonia/DCM) gave the title compound as a pale yellow oil (734 mg).

Example 10

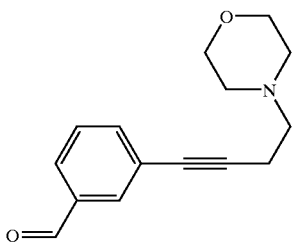

3-(4-Morpholin-4-yl-but-1-ynyl)-benzaldehyde

May be prepared analogously to Example 9 using the product of Example 3.

Example 11

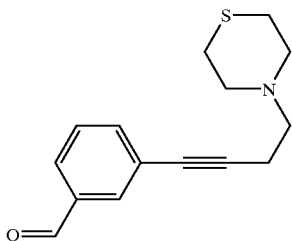

3-(4-Thiomorpholin-4-yl-but-1-ynyl)-benzaldehyde

May be prepared analogously to Example 9 using the product of Example 4.

Example 12

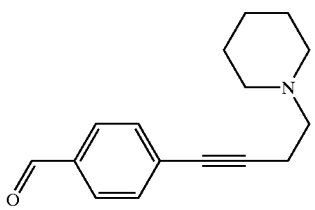

4-(4-Piperidin-1-yl-but-1-ynyl)-benzaldehyde

Method A: To a solution of the product of Example 8 (8.0 g) in 1-butanol (20 mL) was added piperidine (2.4 mL) followed by sodium carbonate (1.3 g) and potassium iodide (81 mg). The resulting mixture was heated at 80° C. for 16 h, cooled to room temperature, diluted with water (200 mL) and extracted with DCM (2×400 mL). The combined organic phases were washed with water (100 mL) and brine (100 mL), dried (magnesium sulfate), and concentrated under reduced pressure. Chromatography of the residue (6–8% 2 M methanolic ammonia/DCM) gave the title compound as a brown oil (4.6 g of a 1:1 mixture of the title compound and 1-[4-(4-Dibutoxymethyl-phenyl)-but-3-ynyl]-piperidine).

Method B: To a mixture of Pd(PPh$_3$)$_2$Cl$_2$ (0.57 g, 0.81 mmol, 0.01 equiv) and CuI (0.31 g, 1.6 mmol, 0.02 equiv), THF (180 mL) and Et$_3$N (90 mL, 0.64 mol, 8.0 equiv) were added under N$_2$. A stream of N$_2$ was bubbled through the solution for 15 min, and then 1-but-3-ynyl-piperidine (11.7 g, 85 mmol, 1.05 equiv) was added. The reaction mixture was stirred at room temperature for 16 h. A white precipitate (Et$_3$N.HBr) was collected by filtration and washed with EtOAc. The filtrate was concentrated under reduced pressure, and the resulting residue was re-dissolved in EtOAc. The EtOAc solution was washed with 1 M NaOH (aq) twice, dried over MgSO$_4$, and then poured directly onto a short pad of silica gel (neutralized with 5% Et$_3$N in hexanes), which was then washed with EtOAc. The filtrate was concentrated under reduced pressure to afford the product as a dark brown oil (18.1 g, 75 mmol, 92%), which was used without further purification (purity>95% by HPLC). MS (electrospray): mass calculated for C$_{16}$H$_{19}$ON, 241.1; m/z found, 242.2 [M+H]$^+$.

Example 13

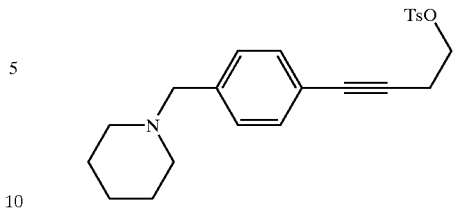

Toluene-4-sulfonic acid 4-(4-piperidin-1-ylmethyl-phenyl)-but-3-ynyl ester

A solution of the product of Example 8 (2.0 g), piperidine (0.91 mL), and acetic acid (0.42 mL) in DCM (100 mL) was treated with sodium triacetoxyborohydride (1.95 g) at room temperature. After 16 h, the resulting mixture was treated with 10% aqueous sodium hydroxide (30 mL). The aqueous phase was extracted with DCM (2×300 mL). The combined organic phases were dried (magnesium sulfate) and concentrated under reduced pressure. The residue was diluted in DCM (100 mL) and passed through a pad of silica gel. The pad was washed with DCM (3×200 mL). The combined filtrate was concentrated under reduced pressure, giving the title compound as a brown oil (2.3 g).

Example 14

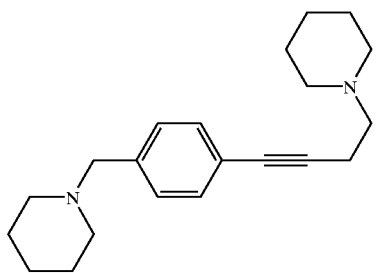

1-[4-(4-Piperidin-1-ylmethyl-phenyl)-but-3-ynyl]-piperidine

K$_i$=1.6 nM

A mixture of the product of Example 1 (254 mg), potassium carbonate (346 mg), copper(I) iodide (7.6 mg), triphenylphosphine (21 mg), 10% palladium on carbon (43 mg) in water (2 mL) and DME (1 mL) was stirred at room temperature for 30 min, and treated with a solution of the product of Example 2 (343 mg) in DME (1 mL). The resulting mixture was heated at 80° C. for 16 h, cooled to room temperature, and filtered through a pad of Celite. The pad was washed with DCM (3×3 mL), and the filtrate was diluted with water (3 mL). The aqueous phase was extracted with DCM (2×3 mL), and the combined organic phases were dried (magnesium sulfate) and concentrated under reduced pressure. Chromatography of the residue (2.5%-5% 2 M methanolic ammonia/DCM) gave the title compound as a colorless oil (88 mg). $^1$H NMR (400 MHz, CDCl$_3$): 7.33 (d, J=7.4 Hz, 2H), 7.22 (d, J=7.8 Hz, 2H), 3.44 (s, 2H), 2.68–2.56 (m, 4H), 2.50–2.43 (m, 4H), 2.39–2.30 (m, 4H), 1.64–1.52 (m, 8H), 1.48–1.38 (m, 4H).

Example 15

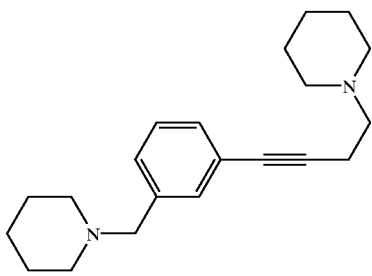

1-[3-(4-Piperidin-1-yl-but-1-ynyl)-benzyl]-piperidine $K_i$=0.8 nM

A solution of the product of Example 9 (193 mg) and piperidine (0.09 mL) in DCE (2 mL) was treated with sodium triacetoxyborohydride (254 mg). After 16 h, the resulting mixture was treated with 10% aqueous potassium hydroxide (2 mL), and extracted with DCM (2×3 mL). The combined organic phases were dried (magnesium sulfate) and concentrated under reduced pressure. Chromatography of the residue (0–8% 2 M methanolic ammonia/DCM) gave the title compound as a pale yellow oil (65 mg). $^1$H NMR (400 MHz, CDCl$_3$): 7.35 (br s, 1H), 7.28–7.21 (m, 3H), 3.42 (s, 2H), 2.67–2.57 (m, 4H), 2.50–2.43 (m, 4H), 2.39–2.31 (m, 4H), 1.63–1.53 (m, 8H), 1.48–1.38 (m, 4H).

Example 16

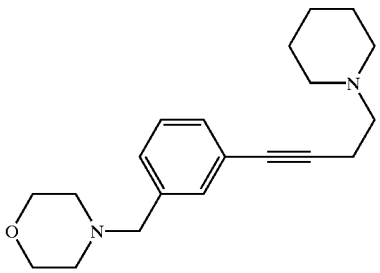

4-[3-(4-Piperidin-1-yl-but-1-ynyl)-benzyl]-morpholine $K_i$=0.8 nM

Method A: A solution of the product of Example 9 (193 mg) and morpholine (0.08 mL) in DCE (2 mL) was treated with sodium triacetoxyborohydride (254 mg). After 16 h, the resulting mixture was treated with 10% aqueous potassium hydroxide (2 mL), and extracted with DCM (2×3 mL). The combined organic phases were dried (magnesium sulfate) and concentrated under reduced pressure. Chromatography of the residue (0–8% 2 M methanolic ammonia/DCM) gave the title compound as a pale yellow oil (188 mg). $^1$H NMR (400 MHz, CDCl$_3$): 7.36 (br s, 1 H), 7.30–7.22 (m, 3H), 3.70 (t, J=4.6 Hz, 4H), 3.45 (s, 2H), 2.68–2.57 (m, 4H), 2.51–2.40 (m, 8H), 1.64–1.57 (m, 4H), 1.48–1.41 (m, 2H).

Method B: A 500-mL, 3-necked round-bottom flask was equipped with a magnetic stirring bar, an addition funnel, a thermometer, and a rubber septum with a nitrogen inlet. The vessel was charged with piperidine (54 mL) and anhydrous ethanol (25 mL). The solution was cooled to 0° C. in an ice bath, and a solution of the product of Example 7 (17.5 g) in anhydrous ethanol (30 mL) was added. The ice bath was removed, and the reaction mixture was allowed to warm to room temperature. After 14 h when the reaction was judged complete by HPLC, the reaction mixture was transferred to a 500 mL round-bottom flask and concentrated under reduced pressure to dryness under reduced pressure. The residue was dissolved in CH$_2$Cl$_2$ (300 mL), washed with 5% aq. NaOH (75 mL), dried over MgSO$_4$, and filtered. The filtrate was concentrated under reduced pressure to give an oil (20 g), which was determined by HPLC and $^1$H NMR to contain an 85:15 mixture of the title compound and 4-(3-pent-4-en-1-ynyl-benzyl)-morpholine.

Example 17

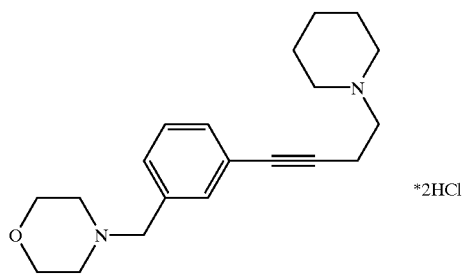

4-[3-(4-Piperidin-1-yl-but-1-ynyl)-benzyl]-morpholine dihydrochloride

A 3-L, 3-necked round-bottom flask was charged with the product of Example 16, Method B (77.0 g, 0.25 mol). To this was added absolute EtOH (385 mL). The reaction mixture was stirred and cooled to ~0° C. in an ice bath. HCl in dioxane (4 N, 126.5 mL) was added drop-wise over 0.5 h. The ice bath was removed, and the reaction mixture was stirred at room temperature for 2 h. The viscous reaction mixture was transferred to a 500 mL addition funnel and then added in a slow, steady stream to a 3-L, 3-necked round-bottom flask containing ether (500 mL), as the flask contents were stirred. The addition funnel was rinsed with absolute EtOH (115 mL), which was subsequently added to the ether solution. Ether (500 mL) was added via an addition funnel in a slow, steady stream. This resulted in the formation of a pale tan precipitate. The suspension was stirred at room temperature for 12 h. More ether (500 mL) was added, and the suspension was cooled to 0° C. and held at that temperature while stirred for 3 h. The product was collected by suction filtration using a medium porosity glass frit (filtration was slow). The filter cake was broken and washed with absolute EtOH/Et$_2$O (1:3, 2×75 mL). The product was dried under house vacuum and, subsequently, in a vacuum oven at 35° C. for 24 h. The dihydrochloride salt was obtained as an off-white powder (80.7 g). HPLC and $^1$H-NMR indicated the product to be >95% pure. A 2-L, 3-necked round-bottom flask equipped with an addition funnel, a reflux condenser and a mechanical stirrer was charged with the crude dihydrochloride salt (80.0 g). Absolute EtOH (160 mL) was added, and the resulting suspension was warmed to ~50° C. Ether (320 mL) was added in a slow stream via the addition funnel. Heating was discontinued, and the suspension slowly cooled to room temperature with stirring over ~4 h. The flask was cooled in an ice bath, stirred, and maintained at 0–5° C. for ~3 h. The precipitate was collected by suction filtration using a medium porosity glass frit (filtration was slow). The filter cake was broken and washed with cold EtOH/Et$_2$O (1:2, 2×75 mL). The product was dried in vacuo at 35° C. The title compound was obtained as an off white powder (76.2). $^1$H NMR (400 MHz, MeOH): 1.56 (bm, 1 H), 1.82–1.85 (m, 3 H), 1.96–1.99 (m, 2 H), 2.99–3.07 (m, 4 H), 3.17–3.24 (m, 2 H), 3.30–3.41 (m, 6 H), 3.62 (bd, J=12.7 Hz, 2 H), 3.79 (bt, J=12.6 Hz, 2 H), 4.01 (bd, J=12.5 Hz, 2 H), 4.37 (s, 2 H), 7.46–7.69 (m, 1 H). 7.53–7.56 (m, 2 H), 7.25 (m, 1 H).

Example 18

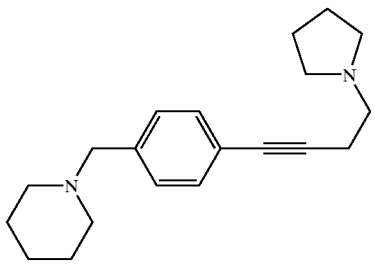

1-[4-(4-Pyrrolidin-1-yl-but-1-ynyl)-benzyl]-piperidine $K_i$=2.0 nM

A mixture of the product of Example 13 (199 mg), pyrrolidine (0.084 mL), and potassium carbonate (69 mg) in 1:1 ethanol/water (6 mL) was heated at 80° C. for 16 h. The resulting mixture was cooled to room temperature, diluted with water (10 mL), and extracted with DCM (2×100 mL). The combined organic phases were washed with water (20 mL) and brine (20 mL), dried (magnesium sulfate), and concentrated under reduced pressure. Chromatography of the residue (0–5% 2 M methanolic ammonia/DCM) gave the title compound as a pale yellow oil (60 mg). $^1$H NMR (400 MHz, CDCl$_3$): 7.33 (d, J=8.1 Hz, 2H), 7.23 (d, J=8.1 Hz, 2H), 3.44 (s, 2H), 2.78–2.73 (m, 2H), 2.64–2.57 (m, 6H), 2.35 (br s, 4H), 1.82–1.78 (m, 4H), 1.59–1.53 (m, 4H), 1.45–1.40 (m, 2H).

Example 19

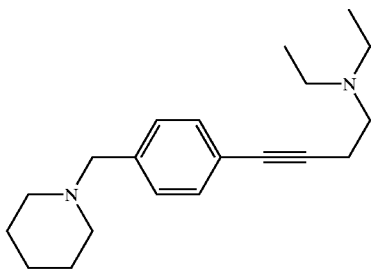

Diethyl-[4-(4-piperidin-1-ylmethyl-phenyl)-but-3-ynyl]-amine $K_i$=2.4 nM

A mixture of the product of Example 13 (199 mg), diethylamine (0.104 mL) and potassium carbonate (69 mg) in 1:1 ethanol/water (6 mL) was heated at 80° C. for 16 h. The resulting mixture was cooled to room temperature, diluted with water (10 mL), and extracted with DCM (2×100 mL). The combined organic phases were washed with water (20 mL) and brine (20 mL), dried (magnesium sulfate), and concentrated under reduced pressure. Chromatography of the residue (0–5% 2 M methanolic ammonia/DCM) gave the title compound as a pale yellow oil (21 mg). $^1$H NMR (400 MHz, CDCl$_3$): 7.33 (d, J=8.0 Hz, 2H), 7.23 (d, J=8.0 Hz, 2H), 3.44 (s, 2H), 2.81–2.73 (m, 2H), 2.64–2.51 (m, 6H), 2.35 (bs, 4H), 1.82–1.78 (m, 3H), 1.59–1.53 (m, 4H), 1.44–1.39 (m, 2H), 1.07 (t, J=7.2 Hz, 3H).

Example 20

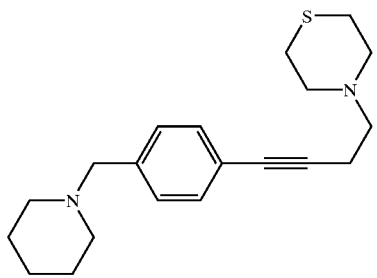

4-[4-(4-Piperidin-1-ylmethyl-phenyl)-but-3-ynyl]-thiomorpholine $K_i$=6.0 nM

A mixture of the product of Example 13 (199 mg), thiomorpholine (0.062 mL) and potassium carbonate (69 mg) in 1:1 ethanol/water (6 mL) was heated at 80° C. for 16 h. The resulting mixture was cooled to room temperature, diluted with water (10 mL) and extracted with DCM (2×100 mL). The combined organic phases were washed with water (20 mL) and brine (20 mL), dried (magnesium sulfate), and concentrated under reduced pressure.

Chromatography of the residue (0–5% 2 M methanolic ammonia/DCM) gave the title compound as a pale yellow oil (27 mg). $^1$H NMR (400 MHz, CDCl$_3$): 7.32 (d, J=8.0 Hz, 2H), 7.23 (d, J=8.1 Hz, 2H), 3.44 (s, 2H), 2.83–2.80 (m, 4H), 2.74–2.68 (m, 6H), 2.59–2.55 (m, 2H), 2.35 (br s, 4H), 1.59–1.53 (m, 4H), 1.44–1.39 (m, 2H).

Example 21

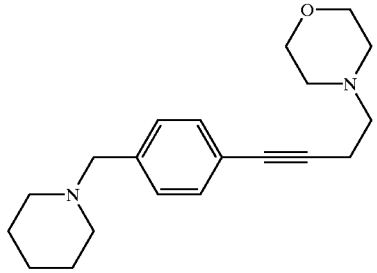

4-[4-(4-Piperidin-1-ylmethyl-phenyl)-but-3-ynyl]-morpholine $K_i$=15 nM

A mixture of the product of Example 13 (199 mg), morpholine (0.052 mL) and potassium carbonate (69 mg) in 1:1 ethanol/water (6 mL) was heated at 80° C. for 16 h. The resulting mixture was cooled to room temperature, diluted with water (10 mL) and extracted with DCM (2×100 mL). The combined organic phases were washed with water (20 mL) and brine (20 mL), dried (magnesium sulfate), and concentrated under reduced pressure. Chromatography of the residue (0–5% 2 M methanolic ammonia/DCM) gave the title compound as a pale yellow oil (40 mg). $^1$H NMR (400 MHz, CDCl$_3$): 7.32 (d, J=8.1 Hz, 2H), 7.23 (d, J=8.0 Hz, 2H), 3.73 (t, J=4.6 Hz, 4H), 3.44 (s, 2H), 2.72–2.58 (m, 4H), 2.54 (t, J=4.5 Hz, 4H), 2.35 (br s, 4H), 1.59–1.53 (m, 4H), 1.44–1.40 (m, 2H).

Example 22

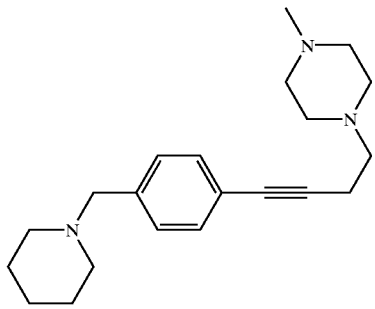

1-Methyl-4-[4-(4-piperidin-1-ylmethyl-phenyl)-but-3-ynyl]-piperazine

K$_i$=21 nM

A mixture of the product of Example 13 (199 mg), 1-methylpiperazine (0.067 mL) and potassium carbonate (69 mg) in 1:1 ethanol/water (6 mL) was heated at 80° C. for 16 h. The reaction mixture was cooled to room temperature. Water (10 mL) was added, and the mixture was extracted with DCM (2×100 mL). The combined organic phases were washed with water (20 mL) and brine (20 mL), dried (magnesium sulfate), and concentrated under reduced pressure. Chromatography of the residue (0–5% 2 M methanolic ammonia/DCM) gave the title compound as a white solid (13 mg). $^1$H NMR (400 MHz, CDCl$_3$): 7.32 (d, J=8.1 Hz, 2H), 7.23 (d, J=8.1 Hz, 2H), 3.44 (s, 2H), 2.71–2.46 (m, 12H), 2.35 (br s, 4H), 2.30 (s, 3H), 1.59–1.53 (m, 4H), 1.45–1.38 (m, 2H).

Example 23

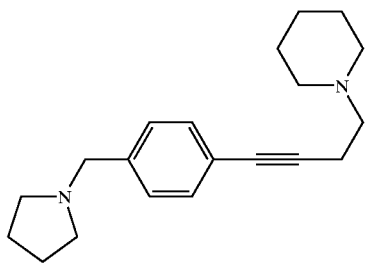

1-[4-(4-Pyrrolidin-1-ylmethyl-phenyl)-but-3-ynyl]-piperidine

K$_i$=1.4 nM

A solution of the product of Example 12 (241 mg), pyrrolidine (0.125 mL) and acetic acid (0.067 mL) in DCM (2 mL) was treated with sodium triacetoxyborohydride (318 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concentrated under reduced pressure. Chromatography of the residue (0.5–5.5% 2 M methanolic ammonia/DCM) gave the title compound as a colorless oil (73 mg). $^1$H NMR (400 MHz, CDCl$_3$): 7.34 (d, J=8.0 Hz, 2H), 7.24 (d, J=8.0 Hz, 2H), 3.58 (s, 2H), 2.68–2.57 (m, 4H), 2.50–2.45 (m, 8H), 1.79–1.76 (m, 4H), 1.63–1.57 (m, 4H), 1.47–1.41 (m, 2H).

Example 24

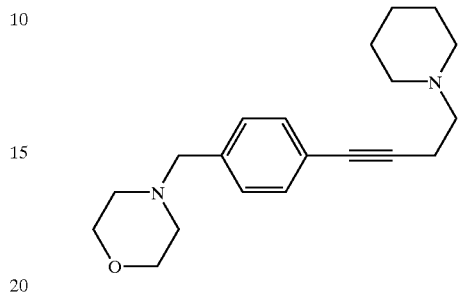

4-[4-(4-Piperidin-1-yl-but-1-ynyl)-benzyl]-morpholine

K$_i$=5.5 nM

A solution of the product of Example 12 (241 mg), morpholine (0.131 mL) and acetic acid (0.067 mL) in DCM (2 mL) was treated with sodium triacetoxyborohydride (318 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concentrated under reduced pressure. Chromatography of the residue (0.5–5.5% 2 M methanolic ammonia/DCM) gave the title compound as a yellow oil (53 mg). $^1$H NMR (400 MHz, CDCl$_3$): 7.34 (d, J=8.2 Hz, 2H), 7.24 (d, J=8.2 Hz, 2H), 3.70 (t, J=4.6 Hz, 4H), 3.47 (s, 2H), 2.68–2.57 (m, 4H), 2.50–2.41 (m, 8H), 1.63–1.57 (m, 4H), 1.48–1.42 (m, 2H).

Example 25

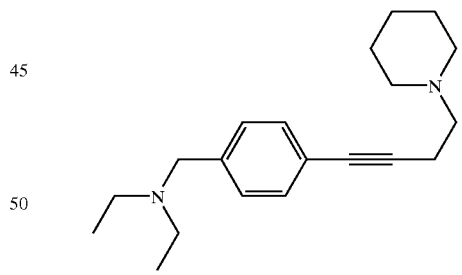

Diethyl-[4-(4-piperidin-1-yl-but-1-ynyl)-benzyl]-amine

K$_i$=1.1 nM

A solution of the product of Example 12 (241 mg), diethylamine (0.155 mL) and acetic acid (0.067 mL) in DCM (2 mL) was treated with sodium triacetoxyborohydride (318 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concen- trated under reduced pressure. Chromatography of the residue (0.5–5.5% 2 M methanolic ammonia/DCM) gave the title compound as a colorless oil (61 mg). ¹H NMR (400 MHz, CDCl₃): 7.33 (d, J=8.1 Hz, 2H), 7.24 (d, J=8.0 Hz, 2H), 3.53 (s, 2H), 2.68–2.57 (m, 4H), 2.52–2.45 (m, 8H), 1.63–1.57 (m, 4H), 1.47–1.41 (m, 2H), 1.02 (t, J=7.1 Hz, 6H).

Example 26

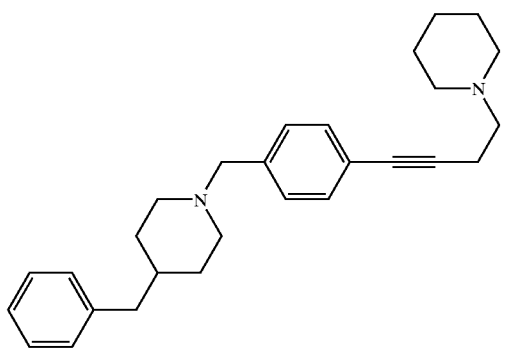

1-{4-[4-(4-Benzyl-piperidin-1-ylmethyl)-phenyl]-but-3-ynyl}-piperidine

K$_i$=2.9 nM

A solution of the product of Example 12 (241 mg), 4-benzylpiperidine (0.264 mL) and acetic acid (0.067 mL) in DCM (2 mL) was treated with sodium triacetoxyborohydride (318 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concentrated under reduced pressure. Chromatography of the residue (0.5–5.5% 2 M methanolic ammonia/DCM) gave the title compound as a white solid (80 mg). ¹H NMR (400 MHz, CDCl₃): 7.32 (d, J=8.0 Hz, 2H), 7.28–7.15 (m, 5H), 7.12 (d, J=7.1 Hz, 2H), 3.43 (s, 2H), 2.83–2.80 (d, J=11.5 Hz, 2H), 2.68–2.56 (m, 4H), 2.52 (d, 7.0 Hz, 2H), 2.46 (br s, 4H), 1.87 (t, J=9.9 Hz, 2H), 1.62–1.57 (m, 6H), 1.53–1.41 (m, 3H), 1.34–1.24 (m, 2H)

Example 27

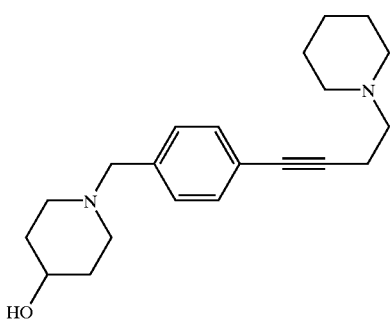

1-[4-(4-Piperidin-1-yl-but-1-ynyl)-benzyl]-piperidin-4-ol

K$_i$=1.7 nM

A solution of the product of Example 12 (241 mg), 4-hydroxypiperidine (152 mg) and acetic acid (0.067 mL) in DCM (2 mL) was treated with sodium triacetoxyborohydride (318 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concentrated under reduced pressure. Chromatography of the residue (0.5–5.5% 2 M methanolic ammonia/DCM) gave the title compound as a colorless oil (60 mg). ¹H NMR (400 MHz, CDCl₃): 7.34 (d, J=8.0 Hz, 2H), 7.22 (d, J=8.0 Hz, 2H), 3.72–3.65 (m, 1H), 3.47 (s, 2H), 2.75–2.57 (m, 6H), 2.47 (br s, 4H), 2.13 (t, J=9.6 Hz, 2H), 1.90–1.84 (m, 2H), 1.63–1.53 (m, 5H), 1.47–1.41 (m, 3H).

Example 28

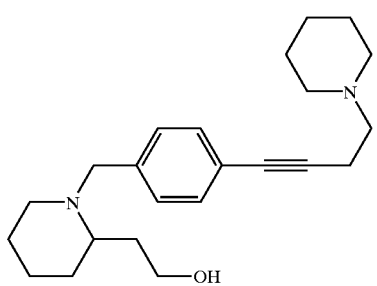

2-{1-[4-(4-Piperidin-1-yl-but-1-ynyl)-benzyl]-piperidin-2-yl}-ethanol

K$_i$=0.4 nM

A solution of the product of Example 12 (241 mg), 2-piperidinoethanol (194 mg) and acetic acid (0.067 mL) in DCM (2 mL) was treated with sodium triacetoxyborohydride (318 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concentrated under reduced pressure. Chromatography of the residue (0.5–5.5% 2 M methanolic ammonia/DCM) gave the title compound as a colorless oil (9 mg). ¹H NMR (400 MHz, CDCl₃): 7.34 (d, J=8.1 Hz, 2H), 7.22 (d, J=8.0 Hz, 2H), 4.15 (d, J=13.1 Hz, 1H), 3.95–3.90 (m, 1H), 3.77–3.71 (m, 1H), 3.43 (d, J=13.0 Hz,1 H), 2.96–2.90 (m,1 H), 2.74–2.57 (m, 7H), 2.47 (br s, 5H), 2.20–2.12 (m, 1H), 1.97–1.25 (m, 11H)

Example 29

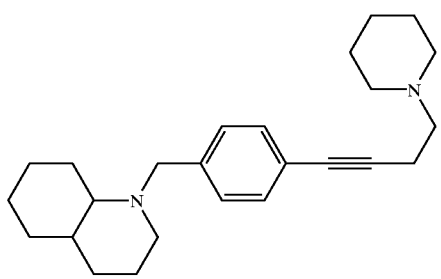

1-[4-(4-Piperidin-1-yl-but-1-ynyl)-benzyl]-decahydro-quinoline

K$_i$=0.8 nM

A solution of the product of Example 12 (241 mg), decahydroquinoline (0.224 mL) and acetic acid (0.067 mL)

in DCM (2 mL) was treated with sodium triacetoxyborohydride (318 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concentrated under reduced pressure. Chromatography of the residue (0.5–5.5% 2 M methanolic ammonia/DCM) gave the title compound as a colorless oil (29 mg). $^1$H NMR (400 MHz, CDCl$_3$): 7.32 (d, J=8.0 Hz, 2H), 7.21 (d, J=8.0 Hz, 2H), 4.03 (d, J=13.7Hz, 1H), 3.19 (d, J=13.7 Hz, 1H), 2.77 (d, J=11.1 Hz, 1H), 2.68–2.57 (m, 5H), 2.47 (brs, 5H), 2.23–2.18 (m, 1H), 1.95–0.83 (m, 18H).

Example 30

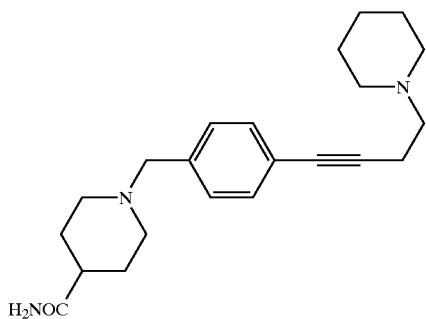

1-[4-(4-Piperidin-1-yl-but-1-ynyl)-benzyl]-piperidine4-carboxylic acid amide $K_i$=1.6 nM A solution of the product of Example 12 (241 mg), isonipecotamide (192 mg) and acetic acid (0.067 mL) in DCM (2 mL) was treated with sodium triacetoxyborohydride (318 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concentrated under reduced pressure. Chromatography of the residue (0.5–5.5% 2 M methanolic ammonia/DCM) gave the title compound as a white solid (87 mg). $^1$H NMR (400 MHz, CDCl$_3$): 7.33 (d, J=8.0 Hz, 2H), 7.23 (d, J=8.0 Hz, 2H), 3.94 (s, 2H), 3.49 (s, 2H), 2.67–2.57 (m, 4H), 2.51–2.45 (m, 8H), 1.77–1.71 (m, 5H), 1.63–1.57 (m, 4H), 1.47–1.42 (m, 2H).

Example 31

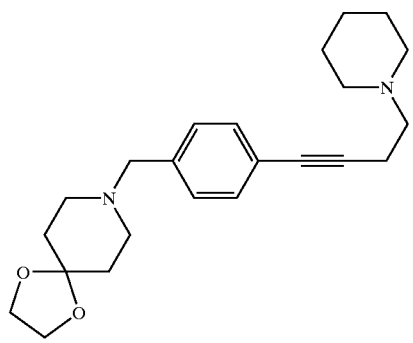

8-[4-(4-Piperidin-1-yl-but-1-ynyl)-benzyl]-1,4-dioxa-8-aza-spiro[4.5]decane $K_i$=1.8 nM A solution of the product of Example 12 (241 mg), 1,4-dioxa-8-azaspiro[4.5]decane (0.192 mL) and acetic acid (0.067 mL) in DCM (2 mL) was treated with sodium triacetoxyborohydride (318 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concentrated under reduced pressure. Chromatography of the residue (0.5–5.5% 2 M methanolic ammonia/DCM) gave the title compound as a colorless oil (108 mg). $^1$H NMR (400 MHz, CDCl$_3$): 7.33 (d, J=8.1 Hz, 2H), 7.22 (d, J=8.1 Hz, 2H), 5.45 (br s, 1 H), 5.31 (br s, 1H), 3.46 (s, 2H), 2.92–2.87 (m, 2H), 2.68–2.57 (m, 4H), 2.47 (brs, 4H), 2.19–2.11 (m, 1H), 2.02–1.95 (m, 2H), 1.87–1.83 (m, 2H), 1.79–1.57 (m, 7H), 1.47–1.41 (m, 2H).

Example 32

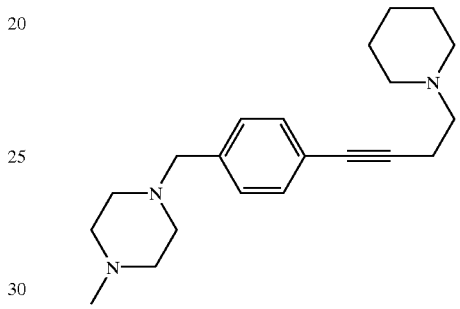

1-Methyl-4-[4-(4-piperidin-1-yl-but-1-ynyl)-benzyl]-piperazine $K_i$=0.7 nM

A solution of the product of Example 12 (241 mg), 1-methylpiperazine (0.166 mL) and acetic acid (0.067 mL) in DCM (2 mL) was treated with sodium triacetoxyborohydride (318 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concentrated under reduced pressure. Chromatography of the residue (0.5–5.5% 2 M methanolic ammonia/DCM) gave the title compound as a colorless oil (65 mg). $^1$H NMR (400 MHz, CDCl$_3$): 7.33 (d, J=8.2 Hz, 2H), 7.23 (d, J=8.2 Hz, 2H), 3.47 (s, 2H), 2.68–2.57 (m, 4H), 2.47 (br s, 12H), 2.28 (s, 3H), 1.62–1.57 (m, 4H), 1.47–1.41 (m, 2H).

Example 33

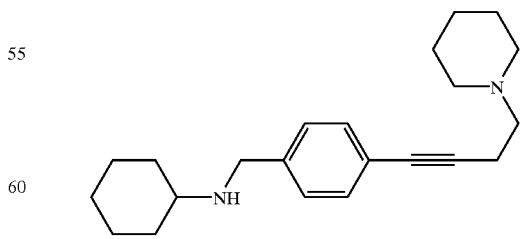

Cyclohexyl-[4-(4-piperidin-1-yl-but-1-ynyl)-benzyl]-amine $K_i$=0.5 nM

A solution of the product of Example 12 (241 mg), cyclohexylamine (0.172 mL), and acetic acid (0.067 mL) in DCM (2 mL) was treated with sodium triacetoxyborohydride (318 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concentrated under reduced pressure. Chromatography of the residue (0.5–5.5% 2 M methanolic ammonia/DCM) gave the title compound as a colorless oil (95 mg). $^1$H NMR (400 MHz, CDCl$_3$): 7.34 (d, J=8.0 Hz, 2H), 7.23 (d, J=8.0 Hz, 2H), 3.79 (s, 2H), 2.68–2.57 (m, 4H), 2.49–2.40 (m, 5H), 1.92–1.86 (m, 2H), 1.76–1.69 (m, 2H), 1.62–1.54 (m, 4H), 1.47–1.41 (m, 2H), 1.29–1.05 (m, 6H).

Example 34

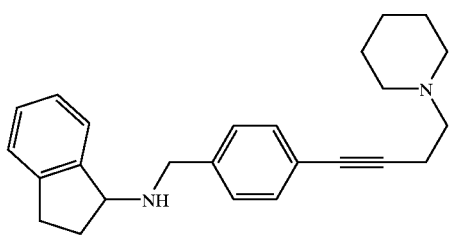

Indan-1-yl-[4-(4-piperidin-1-yl-but-1-ynyl)-benzyl]-amine $K_i$=1.3nM

A solution of the product of Example 12 (241 mg), 1-aminoindian (0.192 mL) and acetic acid (0.067 mL) in DCM (2 mL) was treated with sodium triacetoxyborohydride (318 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concentrated under reduced pressure. Chromatography of the residue (0.5–5.5% 2 M methanolic ammonia/DCM) gave the title compound as a colorless oil (118 mg). $^1$H NMR (400 MHz, CDCl$_3$): 7.37–7.28 (m, 8H), 4.27 (t, 6.6 Hz, 1H), 3.88 (d, 5.6 Hz, 2H), 3.05–2.97 (m, 1H), 2.85–2.77 (m, 1H), 2.68–2.57 (m, 4H), 2.49–2.57 (m, 5H), 1.90–1.82 (m, 1H), 1.63–1.57 (m, 4H), 1.47–1.41 (m, 2H).

Example 35

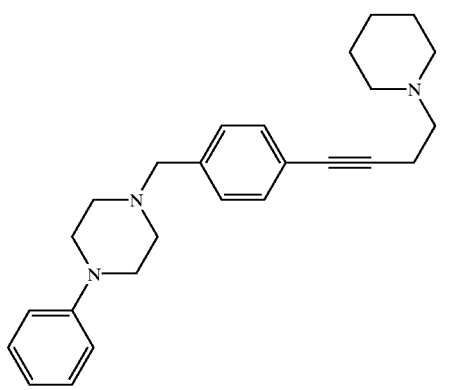

1-Phenyl4-[4-(4-piperidin-1-yl-but-1-ynyl)-benzyl]-piperazine $K_i$=7.0 nM

A solution of the product of Example 12 (241 mg), 1-phenylpiperazine (0.229 mL) and acetic acid (0.067 mL) in DCM (2 mL) was treated with sodium triacetoxyborohydride (318 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concentrated under reduced pressure. Chromatography of the residue (0.5–5.5% 2 M methanolic ammonia/DCM) gave the title compound as a colorless oil (38 mg). $^1$H NMR (400 MHz, CDCl$_3$): 7.17 (d, J=8.0 Hz, 2H), 7.09–7.05 (m, 4H), 6.74 (d, J=8.2 Hz, 2H), 6.67 (t, J=7.4 Hz, 1 H), 3.36 (s, 2H), 3.01 (t, 4.9 Hz, 4H), 2.50–2.39 (m, 8H), 2.29 (br s, 4H), 1.45–1.37 (m, 4H), 1.30–1.23 (m, 2H).

Example 36

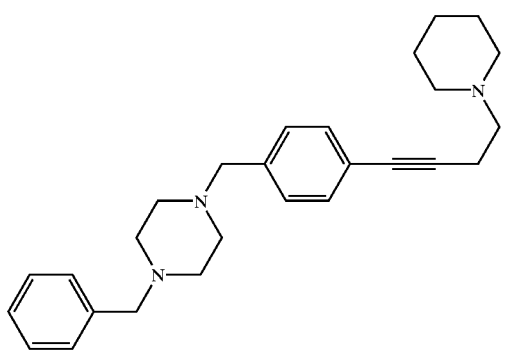

1-Benzyl-4-[4-(4-piperidin-1-yl-but-1-ynyl)-benzyl]-piperazine $K_i$=9.0 nM

A solution of the product of Example 12 (241 mg), 1-benzylpiperazine (0.261 mL) and acetic acid (0.067 mL) in DCM (2 mL) was treated with sodium triacetoxyborohydride (318 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concentrated under reduced pressure. Chromatography of the residue (0.5–5.5% 2 M methanolic ammonia/DCM) gave the title compound as a colorless oil (136 mg). $^1$H NMR (400 MHz, CDCl$_3$): 7.38–7.21 (m, 9H), 3.51 (s, 2H), 3.48 (s, 2H), 2.68–2.56 (m, 4H), 2.46 (br s, 10H), 1.62–1.56 (m, 6H), 1.47–1.42 (m, 2H).

Example 37

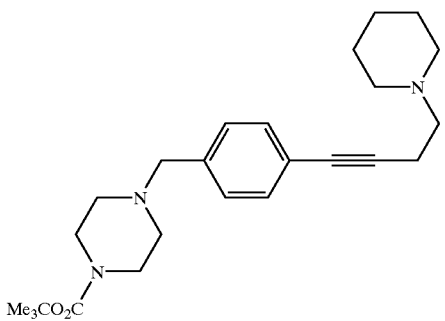

4-[4-(4-Piperidin-1-yl-but-1-ynyl)-benzyl]-piperazine-1-carboxylic acid tert-butyl ester $K_i$=15 nM A solution of the product of Example 12 (241 mg), tert-butyl 1-piperazinecarboxylate (559 mg) and acetic acid (0.067 mL) in DCM (2 mL) was treated with sodium triacetoxyborohydride (318 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concentrated under reduced pressure. Chromatography of the residue (0.5–5.5% 2 M methanolic ammonia/DCM) gave the title compound as a white solid (218 mg). $^1$H NMR (400 MHz, CDCl$_3$): 7.34 (d, J=8.1 Hz, 2H), 7.23 (d, J=8.0 Hz, 2H), 3.48 (s, 2H), 3.43–3.40 (m, 4H), 2.68–2.57 (m, 4H), 2.47 (br s, 4H), 2.36 (br s, 4H), 1.64–1.57 (m, 6H), 1.45 (s, 9H).

Example 38

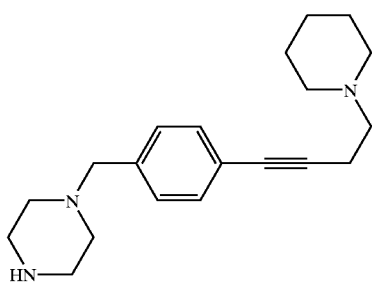

1-[4-(4-Piperidin-1-yl-but-1-ynyl)-benzyl]-piperazine $K_i$=1.3 nM

A solution of the product of Example 37 (184 mg) in 1,4-dioxane (7 mL) was treated with 4 N HCl in 1,4-dioxane at room temperature for 16 h. The solvent was evaporated, and the resulting mixture was treated with 10% aqueous sodium hydroxide (10 mL). The aqueous phase was extracted with 10% methanol in DCM (2×100 mL). The combined organic phases were washed with brine (50 mL), dried (magnesium sulfate), and concentrated under reduced pressure. Chromatography of the residue (1–6% 2 M methanolic ammonia/DCM) gave the title compound as a white solid (97 mg). $^1$H NMR (400 MHz, CDCl$_3$): 7.34 (d, J=8.0 Hz, 2H), 7.23 (d, J=8.0 Hz, 2H), 3.47 (s, 2H), 2.91 (t, J=4.8 Hz, 4H), 2.69–2.58 (m, 4H), 2.48–2.43 (m, 8H), 1.64–1.58 (m, 4H), 1.47–1.41 (m, 2H).

Example 39

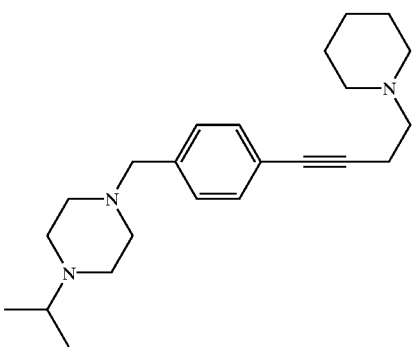

1-Isopropyl-4-[4-(4-piperidin-1-yl-but-1-ynyl)-benzyl]-piperazine $K_i$=1.3 nM

A solution of the product of Example 38 (74 mg), acetone (5 mL) and acetic acid (0.014 mL) in DCM (3 mL) was treated with sodium triacetoxyborohydride (67 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concentrated under reduced pressure. Chromatography of the residue (0.5–5.5% 2 M methanolic ammonia/DCM) gave the title compound as a colorless oil (65 mg). $^1$H NMR (400 MHz, CDCl$_3$): 7.33 (d, J=8.0 Hz, 2H), 7.23 (d, J=8.1 Hz, 2H), 3.48 (s, 2H), 2.68–2.47 (m, 16H), 1.66 (br s, 1H), 1.63–1.57 (m, 4H), 1.48–1.41 (m, 2H), 1.04 (d, J=6.5 Hz, 2H).

Example 40

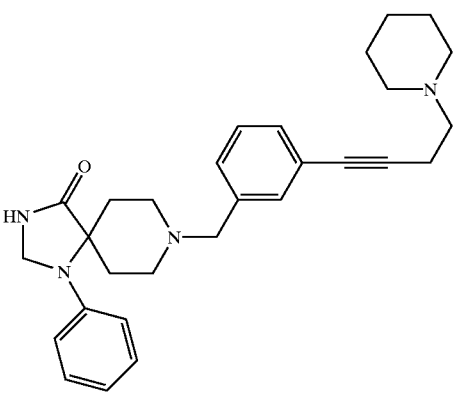

1-Phenyl-8-[3-(4-piperidin-1-yl-but-1-ynyl)-benzyl]-1,3,8-triaza-spiro[4.5]decan-4-one $K_i$=2.0 nM Prepared analogously to Example 15 using 1-phenyl-1,3,8-triaza-spiro[4.5]decan-4-one. $^1$H NMR (400 MHz, CDCl$_3$): 7.41(s, 1H), 7.32–7.21(m, 5H), 6.94–6.85(m, 2H), 4.73(s, 2H), 3.54(s, 2H), 2.84–2.58(m, 10H), 2.47(bs, 4H), 1.65(d, 23.2 Hz, 2H), 1.62–1.58(m, 4H), 1.47–1.43(m, 2H).

Example 41

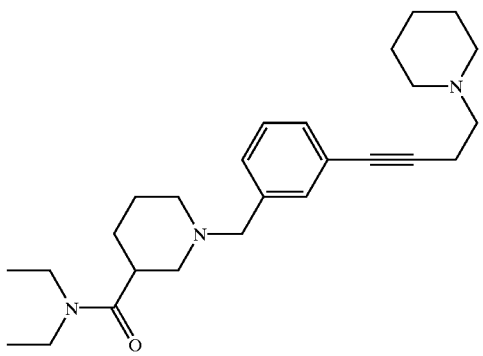

1-[3-(4-Piperidin-1-yl-but-1-ynyl)-benzyl]-piperidine-3-carboxylic acid diethylamide $K_i$=3.0 nM Prepared analogously to Example 15 using piperidine-3-carboxylic acid diethylamide. $^1$H NMR (400 MHz, CDCl$_3$): 7.36(s, 1H), 7.28–7.21(m, 3H), 3.46(s, 2H), 3.38–3.25(m, 4H), 2.87–2.81(m, 2H), 2.75–2.57(m, 5H), 2.46–2.42(m, 4H), 2.19(t, J=11.1 Hz, 1H), 1.99–1.94(m, 1H), 1.77–1.42 (m, 10H), 3.94(t, J=7.1 Hz, 3H), 1.07(t, J=7.1 Hz, 3H).

Example 42

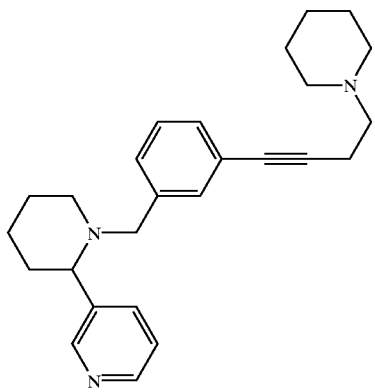

1-[3-(4-Piperidin-1-yl-but-1-ynyl)-benzyl]-1,2,3,4,5,6-hexahydro-[2,3']bipyridinyl $K_i$=11 nM Prepared analogously to Example 15 using 1,2,3,4,5,6-hexahydro-[2,3']bipyridinyl. $^1$H NMR (400 MHz, CDCl$_3$): 8.64 (d, J=2.6 Hz, 1H), 8.50–8.48 (m,1H), 7.80 (d, J=7.9 Hz, 1H), 7.81–7.12(m, 5H), 3.64(d, J=13.5 Hz, 1H), 3.17–3.13 (m, 1H), 2.94(d, J=11.4 Hz, 1H), 2.79(d, J=13.6 Hz, 1H), 2.60–2.58(m, 4H), 2.47(bs, 4H), 1.96–1.90(m, 1H), 1.82–1.75(m, 2H), 1.66–1.39(m, 10H).

Example 43

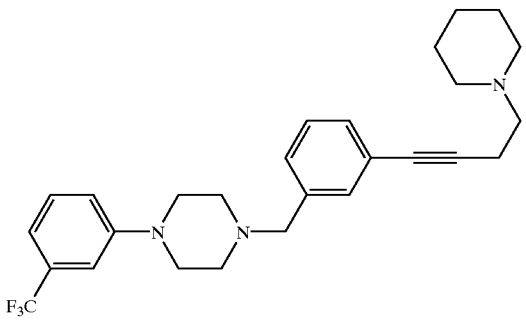

1-[3-(4-Piperidin-1-yl-but-1-ynyl)-benzyl]-4-(3-trifluoromethyl-phenyl)-piperazine $K_i$=91 nM Prepared analogously to Example 15 using 1-(3-trifluoromethyl-phenyl)-piperazine. $^1$H NMR (400 MHz, CDCl$_3$): 7.39(s, 1H), 7.35–7.22(m, 4H), 7.10–7.03(m, 3H), 3.52(s, 2H), 3.24(t, J=5.0 Hz, 4H), 2.69–2.58(m, 8H), 2.47 (bs, 4H), 1.63–1.58(m, 4H), 1.47–1.42(m, 2H).

Example 44

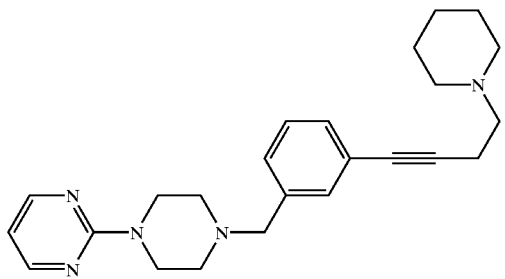

2-{4-[3-(4-Piperidin-1-yl-but-1-ynyl)-benzyl]-piperazin-1-yl}-pyrimidine $K_i$=9.0 nM Prepared analogously to Example 15 using 2-piperazin-1-yl-pyrimidine. $^1$H NMR (400 MHz, CDCl$_3$): 8.29(d, J=4.7 Hz, 2H), 7.39(s, 1 H), 7.31–7.22(m, 3H), 6.46(t, J=4.8 Hz, 1H), 3.82(t, J=5.1 Hz, 4H), 3.50(s, 2H), 2.68–2.58(m, 4H), 2.50–2.47(m, 8H), 1.72–1.57(m, 4H), 1.47–1.41 (m, 2H).

Example 45

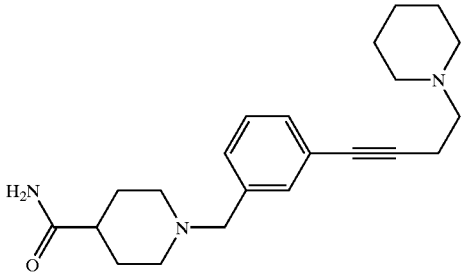

1-[3-(4-Piperidin-1-yl-but-1-ynyl)-benzyl]-piperidine-4-carboxylic acid amide $K_i$=2.0 nM Prepared analogously to Example 15 using piperidine-4-carboxylic acid amide. $^1$H NMR (400 MHz, CDCl$_3$): 8.29 (s,1H), 7.40(s, 1H), 7.31–7.23(m, 3H), 4.38–4.31(m, 1H), 3.52(S, 2H), 3.02(d, 2H), 2.70–2.55(m, 4H), 2.48–2.42(m, 8H), 2.19–2.13(m, 2H), 1.81–1.78(m, 2H)1.63–1.60(m, 2H), 1.46–1.45(m, 2H).

Example 46

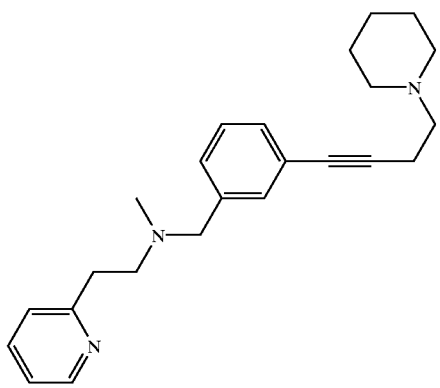

Methyl-[3-(4-piperidin-1-yl-but-1-ynyl)-benzyl]-(2-pyridin-2-yl-ethyl)-amine

K$_i$=4.0 nM

Prepared analogously to Example 15 using methyl-(2-pyridin-2-yl-ethyl)-amine. $^1$H NMR (400 MHz, CDCl$_3$): 8.53–8.51(m, 1H), 7.61–7.56(m, 1H), 7.30–7.09(m, 6H), 3.51(s, 2H), 3.02–2.98(m, 2H), 2.82–2.78(m, 2H), 2.68–2.57(m, 4H), 2.47(bs, 4H), 2.26(s, 3H), 1.63–1.57(m, 4H), 1.47–1.42(m, 2H).

Example 47

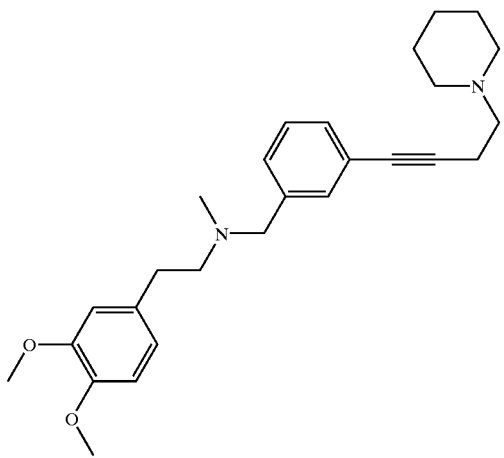

[2-(3,4-Dimethoxy-phenyl)-ethyl]-methyl-[3-(4-piperidin-1-yl-but-1-ynyl)-benzyl]-amine K$_i$=3.0 nM Prepared analogously to Example 15 using [2-(3,4-dimethoxy-phenyl)-ethyl]-methyl-amine. $^1$H NMR (400 MHz, CDCl$_3$): 7.36(s, 1H), 7.29–7.20(m, 3H), 6.80–6.71(m, 3H), 3.86(s, 6H), 3.51(s, 2H), 2.78–2.75(m, 2H), 2.68–2.57 (m, 6H), 2.46(bs, 4H), 2.26(s, 3H), 1.63–1.59(m, 4H), 1.47–1.44(m, 2H).

Example 48

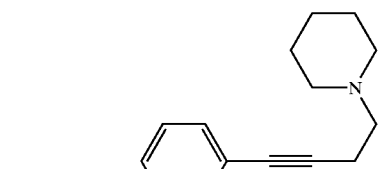

4-[3-(4-Piperidin-1-yl-but-1-ynyl)-benzyl]-thiomorpholine

K$_i$=1.0 nM

Prepared analogously to Example 15 using thiomorpholine. $^1$H NMR (400 MHz, CDCl$_3$): 7.34(s, 1H), 7.29–7.20 (m, 3H), 3.46(s, 2H), 2.69–2.57(m, 12H), 2.47(s, 4H), 1.63–1.57(m, 4H), 1.47–1.42(m, 2H).

Example 49

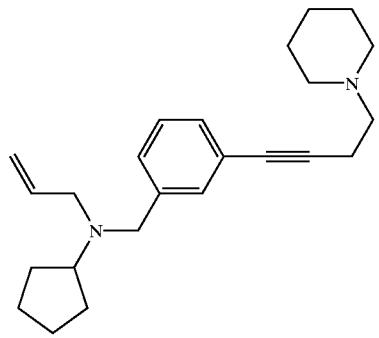

Allyl-cyclopentyl-[3-(4-piperidin-1-yl-but-1-ynyl)-benzyl]-amine

K$_i$=2.0 nM

Prepared analogously to Example 15 using allyl-cyclopentyl-amine. $^1$H NMR (400 MHz, CDCl$_3$): 7.37(s, 1H), 7.26–7.18(m, 3H), 5.94–5.84(m, 1H), 5.16–5.09(m, 2H), 3.57(s, 2H), 3.13–3.07(m, 3H), 2.69–2.57(m, 4H), 2.47(bs, 4H), 1.81–1.75(m, 2H), 1.67–1.43(m, 12H).

Example 50

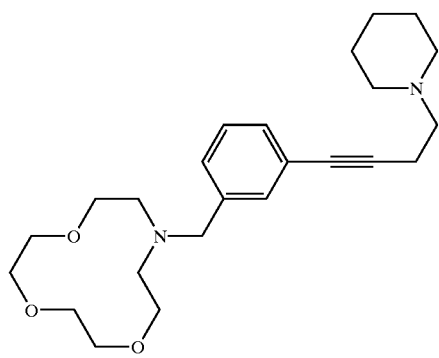

10-[3-(4-Piperidin-1-yl-but-1-ynyl)-benzyl]-1,4,7-trioxa-10-aza-cyclododecane $K_i$=2.0 nM Prepared analogously to Example 15 using 1,4,7-trioxa-10-aza-cyclododecane. $^1$H NMR (400 MHz, CDCl$_3$): 7.38(s, 1H), 7.30–7.19(m, 3H), 3.72–2.69(m, 8H) 3.64–3.62(m, 6H), 2.74(t, J=4.9 Hz, 4H), 2.68–2.58(m, 4H), 2.47(bs, 4H), 1.63–1.57(m, 4H), 1.47–1.43(m, 2H).

Example 51

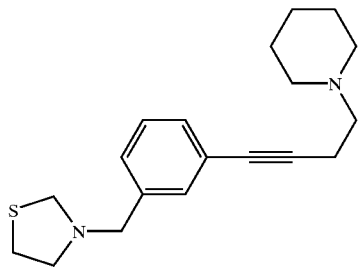

1-[4-(3-Thiazolidin-3-ylmethyl-phenyl)-but-3-ynyl]-piperidine $K_i$=1.0 nM

Prepared analogously to Example 15 using thiazolidine. $^1$H NMR (400 MHz, CDCl$_3$): 7.41(s, 1H), 7.32–7.23(m, 3H), 4.05(s, 2H), 3.51(s, 2H), 3.09(t, J=6.3 Hz, 2H), 2.95(t, J=6.4 Hz, 2H), 2.68–2.58(m, 4H), 2.47(bs, 4H), 1.63–1.58 (m, 4H), 1.47–1.43(m, 2H).

Example 52

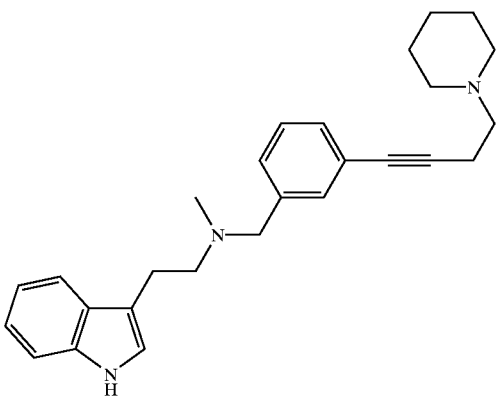

[2-(1H-Indol-3-yl)-ethyl]-methyl-[3-(4-piperidin-1-yl-but-1-ynyl)-benzyl]-amine $K_i$=2.0 nM Prepared analogously to Example 15 using [2-(1H-indol-3-yl)-ethyl]-methyl-amine. $^1$H NMR (400 MHz, CDCl$_3$): 8.11 (s, 1H), 7.55(d, 1H), 7.36–7.01 (m, 8H), 3.54(s, 2H), 3.00–2.96(m, 2H), 2.75–2.58(m, 6H), 2.48(bs, 4H), 2.32(s, 3H), 1.63–1.59(m, 4H), 1.47–1.43(m, 2H).

Example 53

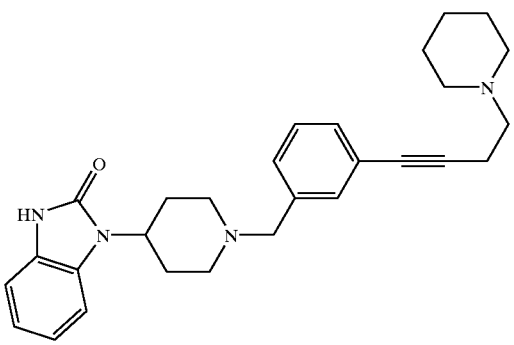

1-{1-[3-(4-Piperidin-1-yl-but-1-ynyl)-benzyl]-piperidin-4-yl}-1,3-dihydro-benzoimidazol-2-one $K_i$=1.0 nM Prepared analogously to Example 15 using 1-piperidin-4-yl-1,3-dihydro-benzoimidazol-2-one. $^1$H NMR (400 MHz, CDCl$_3$): 7.35(s, 1H), 7.29–7.21(m, 3H), 5.41(d, 30.1 Hz, 2H), 3.45(s, 2H), 2.90(d, J=11.7 Hz, 2H), 2.68–2.57(m, 4H), 2.68–2.57(m, 4H), 2.47(bs, 4H), 2.19–2.11(m, 1H), 2.02–1.96(m, 2H), 1.88–1.63(m, 4H), 1.62–1.57(m, 4H), 1.47–1.42(m, 2H).

Example 54

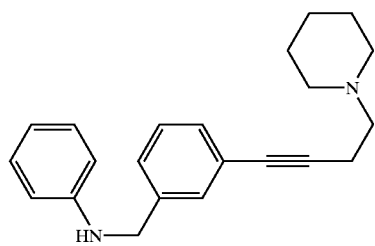

Phenyl-[3-(4-piperidin-1-yl-but-1-ynyl)-benzyl]-amine $K_i$=110 nM

Prepared analogously to Example 15 using aniline. $^1$H NMR (400 MHz, CDCl$_3$): 7.41(s, 1H), 7.40–7.24(m, 3H), 7.19–7.15(m, 2H), 6.72(t, J=7.3 Hz, 1H), 6.63–6.61 (m, 2H), 4.29(d, J=5.2 Hz, 2H), 4.03(bs, 1H), 2.68–2.57(m, 4H), 2.46(bs, 4H), 2.18(s, 1H), 1.62–1.57(m, 4H), 1.47–1.44(m, 2H).

Example 55

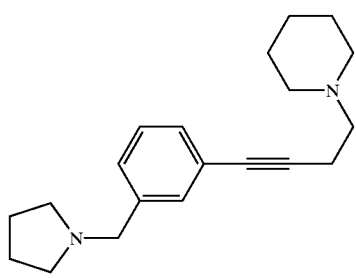

1-[4-(3-Pyrrolidin-1-ylmethyl-phenyl)-but-3-ynyl]-piperidine $K_i$=1.0 nM

Prepared analogously to Example 15 using pyrrolidine. $^1$H NMR (400 MHz, CDCl$_3$): 7.37(s, 1H), 7.28–7.22(m, 3H), 3.56(s, 2H), 2.68–2.57(m, 4H), 2.51–2.46(m, 8H), 1.79–1.76(m, 4H), 1.70–1.57(m, 4H), 1.47–1.43(m, 2H).

Example 56

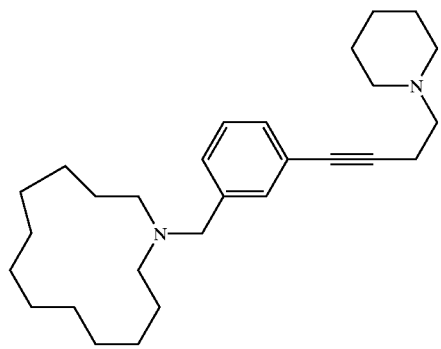

1-[3-(4-Piperidin-1-yl-but-1-ynyl)-benzyl]-azacyclotridecane $K_i$=13 nM

Prepared analogously to Example 15 using azacyclotridecane. $^1$H NMR (400 MHz, CDCl$_3$): 7.37(s, 1H), 7.28–7.19 (m, 3H), 3.43(s, 2H), 2.50(bs, 4H), 2.36–2.33(m, 8H), 1.65–1.38(m, 26H).

Example 57

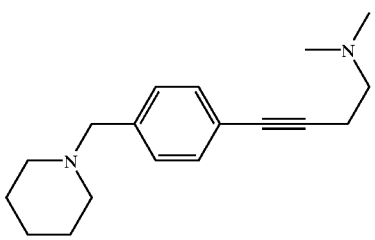

Dimethyl-[4-(4-piperidin-1-ylmethyl-phenyl)-but-3-ynyl]-amine

May be prepared analogously to Example 19 using dimethylamine hydrochloride.

Example 58

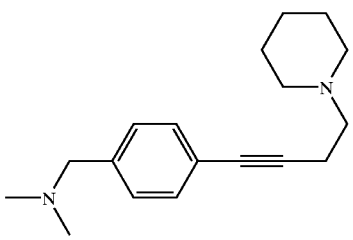

Dimethyl-[4-(4-piperidin-1-yl-but-1-ynyl)-benzyl]-amine

May be prepared analogously to Example 23 using dimethylamine hydrochloride.

Example 59

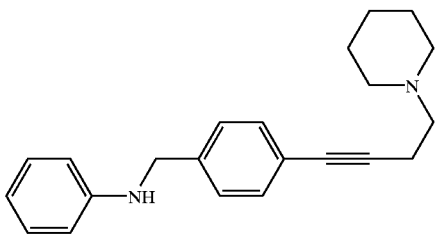

Phenyl-[4-(4-piperidin-1-yl-but-1-ynyl)-benzyl]-amine

May be prepared analogously to Example 23 using aniline.

Example 60

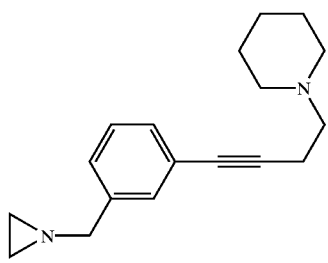

1-[4-(3-Aziridin-1-ylmethyl-phenyl)-but-3-ynyl]-piperidine

May be prepared analogously to Example 15 using aziridine hydrochloride.

Example 61

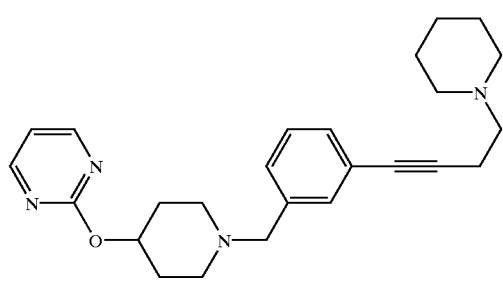

2-{1-[3-(4-Piperidin-1-yl-but-1-ynyl)-benzyl]-piperidin-4-yloxy}-pyrimidine

May be prepared analogously to Example 15 using 2-(piperidin-4-yloxy)-pyrimidine.

Example 62

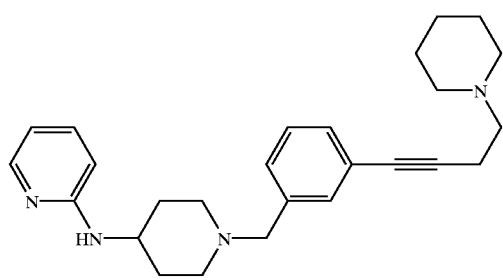

{1-[3-(4-Piperidin-1-yl-but-1-ynyl)-benzyl]-piperidin-4-yl}-pyridin-2-yl-amine

May be prepared analogously to Example 15 using piperidin-4-yl-pyridin-2-yl-amine.

Example 63

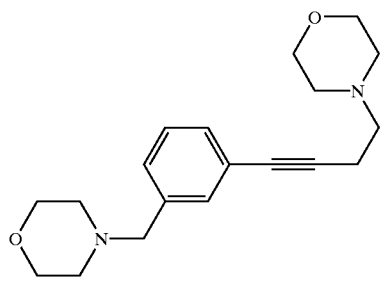

4-[4-(3-Morpholin-4-ylmethyl-phenyl)-but-3-ynyl]-morpholine

May be prepared analogously to Example 15 using the product of Example 10 and morpholine.

Example 64

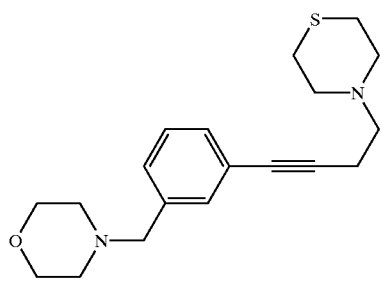

4-[3-(4-Thiomorpholin-4-yl-but-1-ynyl)-benzyl]-morpholine

May be prepared analogously to Example 15 using the product of Example 11 and morpholine.

Example 65

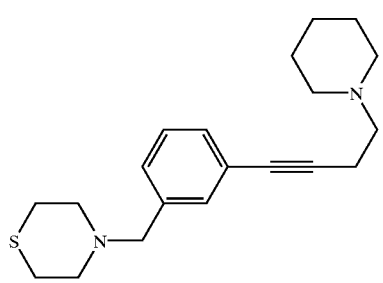

4-[3-(4-Piperidin-1-yl-but-1-ynyl)-benzyl]-thiomorpholine

May be prepared analogously to Example 15 using thiomorpholine.

Example 66

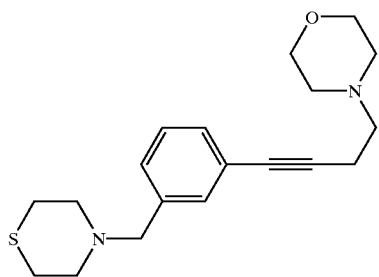

4-[4-(3-Thiomorpholin-4-ylmethyl-phenyl)-but-3-ynyl]-morpholine

May be prepared analogously to Example 15 using the product of Example 10 and thiomorpholine.

Example 67

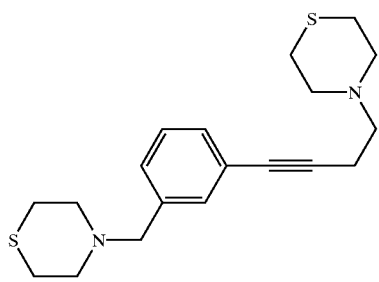

4-[3-(4-Thiomorpholin-4-yl-but-1-ynyl)-benzyl]-thiomorpholine

May be prepared analogously to Example 15 using the product of Example 11 and thiomorpholine.

Example 68

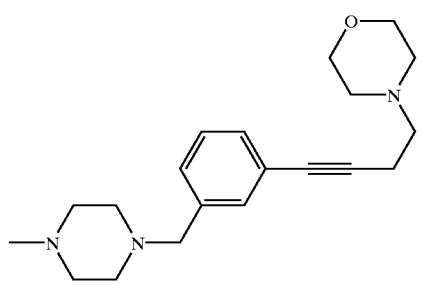

4-{4-[3-(4-Methyl-piperazin-1-ylmethyl)-phenyl]-but-3-ynyl}-morpholine

May be prepared analogously to Example 15 using the product of Example 10 and 1-methylpiperazine.

Example 69

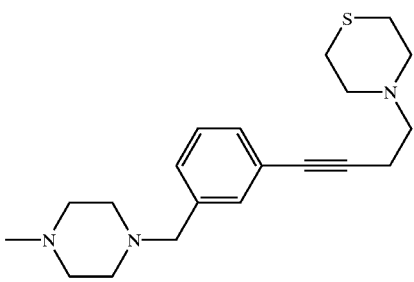

4-{4-[3-(4-Methyl-piperazin-1-ylmethyl)-phenyl]-but-3-ynyl}-thiomorpholine

May be prepared analogously to Example 15 using the product of Example 11 and 1-methylpiperazine.

Example 70

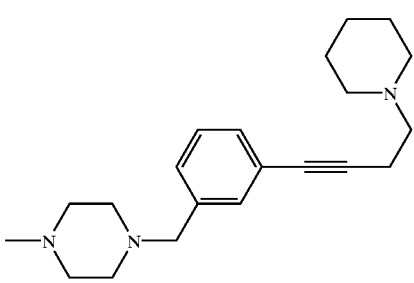

1-Methyl-4-[3-(4-piperidin-1-yl-but-1-ynyl)-benzyl]-piperazine

May be prepared analogously to Example 15 using 1-methylpiperazine.

Example 71

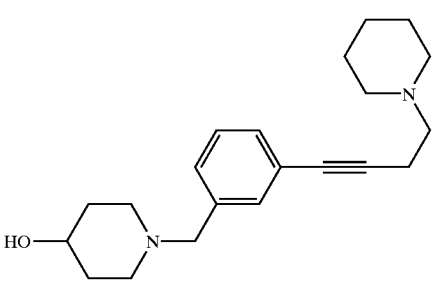

1-[3-(4-Piperidin-1-yl-but-1-ynyl)-benzyl]-piperidin-4-ol

May be prepared analogously to Example 15 using piperidin-4-ol.

Example 72

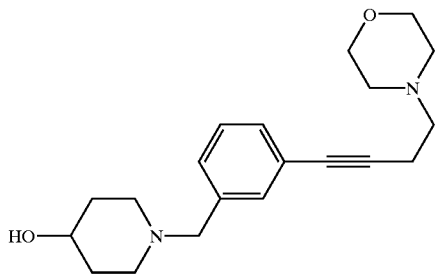

1-[3-(4-Morpholin-4-yl-but-1-ynyl)-benzyl]-piperidin-4-ol

May be prepared analogously to Example 15 using the product of Example 10 and piperidin-4-ol.

Example 73

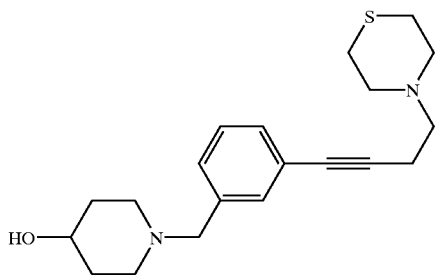

1-[3-(4-Thiomorpholin-4-yl-but-1-ynyl)-benzyl]-piperidin-4-ol

May be prepared analogously to Example 15 using the product of Example 11 and piperidin-4-ol.

Example 74

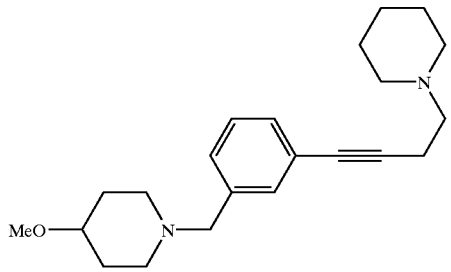

1-{4-[3-(4-Methoxy-piperidin-1-ylmethyl)-phenyl]-but-3-ynyl}-piperidine

May be prepared analogously to Example 15 using 4-methoxypiperidine.

Example 75

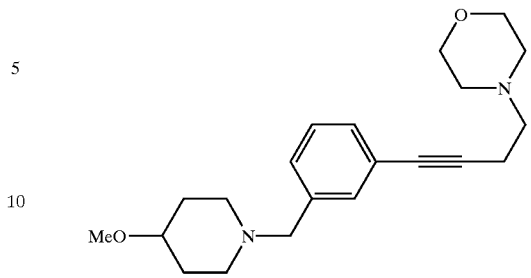

4-{4-[3-(4-Methoxy-piperidin-1-ylmethyl)-phenyl]-but-3-ynyl}-morpholine

May be prepared analogously to Example 15 using the product of Example 10 and 4-methoxypiperidine.

Example 76

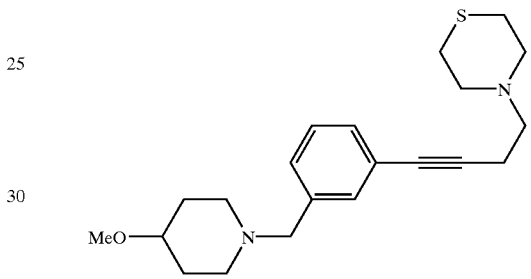

4-{4-[3-(4-Methoxy-piperidin-1-ylmethyl)-phenyl]-but-3-ynyl}-thiomorpholine

May be prepared analogously to Example 15 using the product of Example 11 and 4-methoxypiperidine.

Example 77

Biological Methods

In Vitro

Transfection of Cells with Human Histamine Receptor

A 10 cm tissue culture dish with a confluent monolayer of SK-N-MC cells was split two days prior to transfection. Using sterile technique the media was removed and the cells were detached from the dish by the addition of trypsin. One fifth of the cells were then placed onto a new 10 cm dish. Cells were grown in a 37° C. incubator with 5% $CO_2$ in Minimal Essential Media Eagle with 10% Fetal Bovine Serum. After two days cells were approximately 80% confluent. These were removed from the dish with trypsin and pelleted in a clinical centrifuge. The pellet was then re-suspended in 400 $\mu$L complete media and transferred to an electroporation cuvette with a 0.4 cm gap between the electrodes. One microgram of supercoiled $H_3$ receptor cDNA was added to the cells and mixed. The voltage for the electroporation was set at 0.25 kV, the capacitance was set at 960 $\mu$F. After electroporation the cells were diluted into 10 mL complete media and plated onto four 10 cm dishes. Because of the variability in the efficiency of electroporation, four different concentrations of cells were plated. The ratios used were; 1:20, 1:10, 1:5, with the remainder of the cells being added to the fourth dish. The cells were allowed to recover for 24 hours before adding the selection media (complete media with 600 µg/mL G418). After 10 days dishes were analyzed for surviving colonies of cells. Dishes with well isolated colonies were used. Cells from individual colonies were isolated and tested. SK-N-MC cells were used because they give efficient coupling for inhibition of adenylate cyclase. The clones that gave the most robust inhibition of adenylate cyclase in response to histamine were used for further study.

[$^3$H]-N-methylhistamine Binding

Cell pellets from histamine $H_3$ receptor-expressing SK-N-MC cells were homogenized in 20 mM TrisHCl/0.5 mM EDTA. Supernatants from a 800 g spin were collected, recentrifuged at 30,000 g for 30 min. Pellets were re-homogenized in 50 mM Tris/5 mM EDTA (pH 7.4). Membranes were incubated with 0.8 nM [$^3$H]-N-methylhistamine plus/minus test compounds for 45 min at 25° C. and harvested by rapid filtration over GF/C glass fiber filters (pretreated with 0.3% polyethylenimine) followed by four washes with ice cold buffer. Filters were dried, added to 4 mL scintillation cocktail and then counted on a liquid scintillation counter. Non-specific binding was defined with 10 µM histamine. The $pK_i$ values were calculated based on a $K_d$ of 800 pM and a ligand concentration ([L]) of 800 pM according to the formula:

$$K_i = (IC_{50})/(1+([L]/(K_d)))$$

In Vivo

Elucidation of Oral Absorption and Blood-Brain Barrier Penetration Profiles of $H_3$ Receptor Antagonists in the Rat A rat in vivo system was used to determine the blood-brain barrier penetration profiles and kinetics of various $H_3$ receptor antagonists after single bolus oral administration.

Female Sprague Dawley Rats (~300 gram body weight) were housed in accordance with institutional standards and allowed to acclimate for at least 7 days prior to the study. Each $H_3$ antagonist was formulated in 0.5% hydroxypropylmethyl cellulose at a concentration of 1 mg/mL for oral dosing. The test compound was administered to each of eight animals as a single oral dose of 10 mL/kg (10 mg/kg). Remaining dosing solution was retained for analysis. Two animals from each original group of eight were euthanized via $CO_2$ asphyxiation at t=1, 6, 24, and 48 h. After each animal was euthanized, 0.1 mL of its blood was sampled via cardiac puncture, and its brain was removed via dissection of the cranial bones and placed in a pre-weighed 50 mL conical tube on dry ice.

The blood was added to 0.3 mL of 6% trichloroacetic acid, and the acidified sample was vortexed and then centrifuged (5 min at 14,000 rpm in a microcentrifuge). The clear supernatant was retained for analysis. The frozen brain was weighed, homogenized in 6% trichloroacetic acid (3 mL/g wet weight of tissue), and then centrifuged. The clear supernatant was retained for analysis. The supernatants from the blood and brain samples were analyzed by liquid chromatography with mass spectral detection utilizing selective reaction monitoring (LC-MS/MS). The LC method used a Phenomonex Polar RP column (2×50 mm) and a linear solvent gradient of water and acetonitrile (both 1% in acetic acid).

Graphs of $H_3$ receptor antagonist concentration versus time for blood and brain were generated from the LC-MS/MS results. The mean residency time (MRT) of the $H_3$ receptor antagonist, in blood or in the brain, was calculated from the ratio of the area under the first moment curve (AUMC) to the area under the concentration time curve (AUC): AUMC/AUC. The Blood Brain Barrier index was calculated from the log of $AUC_{brain}/AUC_{blood}$.

F. Other Embodiments

The features and advantages of the invention will be apparent to one of ordinary skill in view of the discussion, examples, embodiments, and claims relating to the invention. The invention also contemplates variations and adaptations, based on the disclosure herein concerning the key features and advantages of the invention, and within the abilities of one of ordinary skill.

What is claimed is:

1. A compound of formula (I)

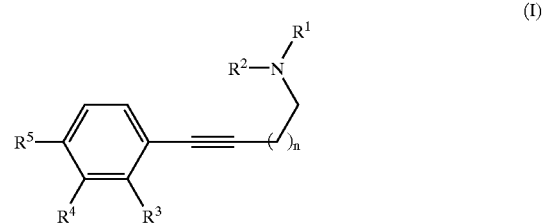

wherein n is an integer from 10 to 1;

$R^1$ and $R^2$ are independently selected from $C_{1-3}$ alkyl, allyl, and $C_{3-8}$ cycloalkyl, or taken together with the nitrogen to which they are attached, they form a non-aromatic 4–7 membered heterocyclyl optionally containing up to two additional heteroatoms independently selected from O, S, and N;

one of $R^3$, $R^4$, and $R^5$ is G, one of the remaining two is hydrogen, and the other is selected from hydrogen, fluoro, and chloro;

G is $L^2Q$;

$L^2$ is methylene;

Q is piperazinyl;

wherein each of the above alkyl, alkylene, alkenyl, heterocyclyl, cycloalkyl, carbocyclyl, and aryl groups of Formula (I) may each be independently and optionally substituted with between 1 and 3 substituents independently selected from methoxy, halo, amino, nitro, hydroxyl, and $C_{1-3}$ alkyl;

and wherein 1–3 substituents of Q can be further independently selected from tert-butyloxycarbonyl, carboxamide, $C_{1-6}$ alkyl, 5–9-membered heterocyclyl, $N(C_{1-6}$ alkyl)(5–9 membered heterocyclyl), NH(5–9 membered heterocyclyl), O(5–9 membered heterocyclyl), (5–9 membered heterocyclyl)$C_{1-3}$ alkylene, phenyl, $C_{1-2}$-hydroxyalkylene, $C_{2-6}$ alkoxy, $(C_{3-6}$ cycloalkyl)-O—, phenyl, (phenyl)$C_{1-3}$ alkylene, and (phenyl)$C_{1-3}$ alkylene-O— and where said substituent groups of Q may optionally have between 1 and 3 substituents independently selected from trifluoromethyl, halo, nitro, cyano, and hydroxy;

or a pharmaceutically acceptable salt, ester, or amide thereof.

2. A compound of claim 1, wherein $NR^1R^2$ taken together form piperidinyl, methylpiperidinyl, dimethylamino, pyrrolidinyl, diethylamino, methylethylamino, ethylpropylamino, or dipropylamino.

3. A compound of claim 2, wherein $NR^1R^2$ taken together form piperidinyl, pyrrolidinyl, or diethylamino.

4. A compound of claim 3, wherein $NR^1R^2$ taken together form piperidinyl or pyrrolidinyl.

5. A compound of claim 1, wherein one of $R^4$ and $R^5$ is G.

6. A compound of claim 5, wherein $R^4$ is G.

7. A compound of claim 5, wherein $R^5$ is G.

8. A compound of claim 1, wherein n is 1.

9. A compound of claim 1, wherein substituted Q is selected from N-($C_{1-6}$ alkyl) piperazinyl, and N-phenyl-piperazinyl.

10. A compound of claim 1, wherein Q is 4-(3-trifluoromethyl-phenyl)-piperazine.

11. A compound of claim 9, wherein Q is substitute with a substituent consisting of a $C_{1-6}$ heterocyclyl group selected from: pyridyl, pyrimidyl, furyl, thiofuryl, imidazolyl, (imidazolyl)$C_{1-6}$ alkylene, oxazolyl, thiazolyl, 2,3-dihydro-indolyl, benzimidazolyl, 2-oxobenzimidazolyl, (tetrazolyl) $C_{1-6}$ alkylene, tetrazolyl, (triazolyl)$C_{1-6}$ alkylene, triazolyl, (pyrrolyl)$C_{1-6}$ alkylene, and pyrrolyl.

12. A compound of claim 1, wherein n is 1;

$R^1$ and $R^2$ are independently selected from $C_2$ alkyl, or taken together with the nitrogen to which they are attached, they form a non-aromatic 5–6 membered heterocyclyl optionally containing an additional heteroatom independently selected from O, S, and N;

one of $R^3$, $R^4$, and $R^5$ is G and the two remaining are H;

G is $L^2Q$;

$L^2$ is methylene;

Q is piperazinyl;

wherein each of the above alkyl, alkylene, alkenyl, alkenylene, heterocyclyl, and carbocyclyl groups may each be independently and optionally substituted with between 1 and 3 substituents selected from methoxy, halo, amino, nitro, hydroxyl, and $C_{1-3}$ alkyl;

and wherein substituents of Q can be further selected from tert-butyloxycarbonyl, carboxamide, 5–9-membered heterocyclyl, NH(6-membered heterocyclyl), O(6-membered heterocyclyl), phenyl, $C_2$-hydroxyalkylene, hydroxy, benzyl and, where each of above heterocyclyl, phenyl, and alkyl substituent group of Q may be optionally substituted with trifluoromethyl.

or a pharmaceutically acceptable salt, ester, or amide thereof.

13. A compound of claim 1, wherein (a) $NR^1R^2$ taken together form piperidinyl, pyrrolidinyl, or diethylamino, and (b) Q is piperazinyl.

14. A compound of claim 1, selected from: 1-methyl-4-[4-(4-piperidin-1-yl-but-1-ynyl)-benzyl]-piperazine; 1-phenyl-4-[4-(4-piperidin-1-yl-but-1-ynyl)-benzyl]-piperazine; 1-benzyl-4-[4-(4-piperidin-1-yl-but-1-ynyl)-benzyl]-piperazine; 4-[4-(4-piperidin-1-yl-but-1-ynyl)-benzyl]-piperazine-1-carboxylic acid tert-butyl ester; 1-[4-(4-piperidin-1-yl-but-1-ynyl)-benzyl]-piperazine; 1-isopropyl-4-[4-(4-piperidin-1-yl-but-1-ynyl)-benzyl]-piperazine; 1-[3-(4-piperidin-1-yl-but-1-ynyl)-benzyl]-4-(3-trifluoromethyl-phenyl)-piperazine; 2-{4-[3-(4-piperidin-1-yl-but-1-ynyl)-benzyl]-piperazin-1-yl }-pyrimidine; 4-{4-[3-(4-methyl-piperazin-1-ylmethyl)-phenyl]-but-3-ynyl}-morpholine; 4-{4-[3-(4-methyl-piperazin-1-ylmethyl)-phenyl]-but-3-ynyl}-thiomorpholine; and 1-methyl-4-[3-(4-piperidin-1-yl-but-1-ynyl)-benzyl]-piperazine.

15. A compound of claim 1, selected from: 1-methyl-4-[4-(4-piperidin-1-yl-but-1-ynyl)-benzyl]-piperazine; 1-[4-(4-piperidin-1-yl-but-1-ynyl)-benzyl]-piperazine; and 1-isopropyl-4-[4-(4-piperidin-1-yl-but-1-ynyl)-benzyl]-piperazine.

16. A compound of claim 1, selected from: 1-[3-(4-piperidin-1-yl-but-1-ynyl)-benzyl]-4-(3-trifluoromethyl-phenyl)-piperazine; and 2-{4-[3-(4-piperidin-1-yl-but-1-ynyl)-benzyl]-piperazin-1-yl}-pyrimidine.

17. A compound of claim 1, selected from: 4-{4-[3-(4-methyl-piperazin-1-yl methyl)-phenyl]-but-3-ynyl}-morpholine; 4-{4-[3-(4-methyl-piperazin-1-ylmethyl)-phenyl]-but-3-ynyl}-thiomorpholine; and 1-methyl-4-[3-(4-piperidin-1-yl-but-1-ynyl)-benzyl]-piperazine.

18. A pharmaceutical composition, comprising a compound of claim 1 and a pharmaceutically-acceptable excipient.

19. A method of inhibiting histamine $H_3$ receptor activity in a subject, comprising administering an effective amount of a compound of claim 1 to a subject in need of such inhibition of histamine $H_3$ receptor activity.

20. A method of treating a subject having a disease on condition modulated by histamine $H_3$ receptor activity, comprising administering to the subject a therapeutically effective amount of a compound of claim 1, wherein said disease or condition is selected from the group consisting of migraine, asthma, dementia, epilepsy, narcolepsy, eating disorders, motion sickness, vertigo, schizophrenia, nasal congestion, allergic rhinitis, and upper airway allergic response.

21. A method for treating one or more disorders or conditions selected from the group consisting of narcolepsy, and arousal/vigilance disorders, comprising administering to a subject a therapeutically effective amount of a compound of claim 1.

22. A method for treating one or more disorders or conditions selected from the group consisting schizophrenia, depression, manic disorders, and bipolar disorders comprising administering to a subject a therapeutically effective amount of a compound of claim 1.

23. A method for treating or preventing upper airway allergic response, nasal congestion, and for the treatment of allergic rhinitis, comprising administering to a subject a therapeutically effective amount of a compound of claim 1.

* * * * *

UNITED STATES PATENT AND TRADEMARK OFFICE
CERTIFICATE OF CORRECTION

PATENT NO. : 6,884,803 B2
DATED : April 26, 2005
INVENTOR(S) : Richard Apodaca, Wei Xiao and Jill A. Jablonowski It is certified that error appears in the above-identified patent and that said Letters Patent is hereby corrected as shown below:

Column 62,
Line 22, change "10 to 1" to read -- 0 to 1 --

Signed and Sealed this

Nineteenth Day of July, 2005

JON W. DUDAS
*Director of the United States Patent and Trademark Office*